US012770735B2

(12) United States Patent
Minetti et al.

(10) Patent No.: US 12,770,735 B2
(45) Date of Patent: Oct. 20, 2026

(54) SYSTEM FOR REMOTE GUIDANCE OF MEDICAL PROCEDURES

(71) Applicants: Tyler Paul Minetti, Sparta, NJ (US); Joseph Jon Messner, Emerson, NJ (US)

(72) Inventors: Tyler Paul Minetti, Sparta, NJ (US); Joseph Jon Messner, Emerson, NJ (US)

(73) Assignee: NOPTIC HEALTHCARE LLC, Sparta Township, NJ (US)

( * ) Notice: Subject to any disclaimer, the term of this patent is extended or adjusted under 35 U.S.C. 154(b) by 0 days.

(21) Appl. No.: 19/056,884

(22) Filed: Feb. 19, 2025

(65) Prior Publication Data

US 2025/0329450 A1 Oct. 23, 2025

Related U.S. Application Data

(63) Continuation of application No. 18/642,270, filed on Apr. 22, 2024, now Pat. No. 12,260,959.

(51) Int. Cl.
*G16H 40/67* (2018.01)
*G06F 3/01* (2006.01)
(Continued)

(52) U.S. Cl.
CPC ............. *G16H 40/67* (2018.01); *G06F 3/011* (2013.01); *G06F 3/016* (2013.01); *G06F 3/167* (2013.01); *G16H 20/17* (2018.01); *G16H 80/00* (2018.01)

(58) Field of Classification Search
CPC ........ G16H 40/67; G16H 20/17; G16H 80/00; G16H 40/63; G06F 3/011; G06F 3/016; G06F 3/167
See application file for complete search history.

(56) References Cited

U.S. PATENT DOCUMENTS

| | | | |
|---|---|---|---|
| 9,298,884 | B1 | 3/2016 | Ahmad |
| 10,398,855 | B2 | 9/2019 | Mcclellan |

(Continued)

FOREIGN PATENT DOCUMENTS

| | | | |
|---|---|---|---|
| KR | 20220082965 | A | 6/2022 |

OTHER PUBLICATIONS

International Search Report and Written Opinion for corresponding International Application PCT/US2025/020330 dated Sep. 9, 2025 (14 pages).

*Primary Examiner* — Chinyere Mpamugo
(74) *Attorney, Agent, or Firm* — Botos Churchill IP Law LLP

(57) ABSTRACT

A system for remote guidance of medical procedures enables patients to be remotely trained by a healthcare provider on how to perform a medical procedure. The system implements Augmented Reality (AR) technology to enhance the remote training of the patient by the healthcare provider. The system includes a patient interface subsystem, a provider interface subsystem, a patient communication module, and a provider communication module. The patient interface subsystem includes an AR headset that enhances the training of the patient by providing video feed enhanced with AR instructional elements while simultaneously providing intelligent feedback during the training session. The provider interface subsystem allows the healthcare provider to remotely monitor and communicate with the patient and to provide the appropriate guidance to the patient during the training session. The patient communication module and the provider communication module allow for remote communication between the patient and the healthcare provider during the training session.

20 Claims, 27 Drawing Sheets

(51) Int. Cl.
*G06F 3/16* (2006.01)
*G16H 20/17* (2018.01)
*G16H 80/00* (2018.01)

(56) References Cited

U.S. PATENT DOCUMENTS

2020/0390328 A1* 12/2020 Toth ........................ A61B 18/02
2022/0310253 A1* 9/2022 Ferro, Jr. .............. G06T 19/006

* cited by examiner

SYSTEM FOR REMOTE GUIDANCE OF MEDICAL PROCEDURES

CROSS-REFERENCE TO RELATED APPLICATIONS

This application is a continuation of U.S. application Ser. No. 18/642,270, filed Apr. 22, 2024, the entire disclosure of which is incorporated by reference herein. This application is related to U.S. application Ser. No. 19/056,913, filed Feb. 19, 2025, the entire disclosure of which is incorporated herein by reference.

FIELD OF THE INVENTION

The present invention relates generally to communication and healthcare systems. More specifically, the present invention discloses a system that allows healthcare providers to remotely provide guidance and feedback to train patients to perform a medical procedure.

BACKGROUND OF THE INVENTION

Healthcare has greatly improved during the last decades thanks to technological advancement, especially regarding the safety and effectiveness of medical procedures. Unfortunately, current remote communication systems in healthcare still have limitations on how information can be collected and shared between healthcare providers and patients. Newer systems allow for the sharing of information in various multimedia formats to help the patient understand the healthcare provider's feedback. However, most of the shared information is not catered to the patient whose conditions may require specific feedback from the healthcare provider in real-time. These limitations are worse in situations where the healthcare provider needs to remotely guide the patient on how to perform a medical procedure. For example, patients across the world are forced to perform self-injections from home. This is extremely prevalent for patients who require care from rheumatologists, endocrinologists, allergists, gastroenterologists, or hematologists. Normally, doctors personally give the patient a preliminary injection to assess if there is an allergy. Afterwards, the patient is trained by a nurse from the pharmaceutical company to perform the self-injections at home. Unfortunately, after being referred out, many patients are lost to follow-up. Patients who are lost to follow-up are patients that miss contact from the pharmaceutical company and do not begin their medication accordingly. Therefore, there is a need for a system that allows for information and instructions to be remotely shared between healthcare providers and patients in real-time, especially when providers are guiding patients on how to perform certain medical procedures.

An objective of the present invention is to provide a system for remote guidance of medical procedures that bridges the gap in home healthcare where patients are lost to follow-up post-referral. The present invention facilitates the proper training of patients by remote healthcare providers to perform various medical procedures remotely, such as performing self-injections at home. The present invention supplies healthcare providers and patients with means to remotely communicate and share information in real-time for effective patient training and guidance. Further, the present invention enables the healthcare provider to receive real-time patient information to guide the patient with the appropriate feedback during the medical procedure including, but not limited to, the patient's health conditions, the patient's surroundings, and the available medical supplies for the procedure. In addition, the present invention enables healthcare providers to deliver appropriate feedback and guidance to the user in different formats including, but not limited to, visual, auditory, and haptic cues as well as verbal instructions output in real time to the patient.

Furthermore, the present invention enables the patient to receive feedback and guidance from the healthcare provider in real-time during the training of the medical procedure. The feedback and guidance are presented to the patient in an enhanced format that allows the patient to self-perform the medical procedure while having access to the feedback and guidance from the healthcare provider. For example, the present invention can incorporate Extended Reality (XR) technology to enhance the healthcare provider's guidance to the patient during the medical procedure training. The XR technology can include, but is not limited to, Augmented Reality (AR) technology, Virtual Reality (VR) technology, or Mixed Reality (MR) technology. The implementation of the present invention would provide an increase of reach and efficiency for patient care, enhance patient privacy, provide cost effective nursing support, improve safety for patients with compromised immune systems, and decrease the carbon footprints for pharmaceutical companies. Additional features and benefits of the present invention are further discussed in the sections below.

SUMMARY OF THE INVENTION

The present invention discloses a system for remote guidance of medical procedures. The present invention aims to intervene during the lapse in the continuum of healthcare. In the preferred embodiment, the present invention implements Augmented Reality (AR) to facilitate a professional-guided remote training session where a patient is virtually trained to self-perform different medical procedures, such as performing an injection from the comfort of their home. By utilizing AR, the present invention allows healthcare providers to see the patient's view and guide the patient during the training session. Simultaneously, the patient can view the healthcare provider as an overlay on the AR display from a continuous video feed from the provider's workstation. The present invention further allows the healthcare provider to instruct the AR headset to overlay different visual elements which are displayed to the patient to guide the medical procedure. The visual elements can include, but are not limited to, cues, instructions, or feedback that can be output in different forms such as in visual form, auditory form, haptic form, etc. The present invention can further include different means for the healthcare provider to introduce the cues, instructions, or feedback into the system. For example, the present invention can include different input devices including, but not limited to, a keyboard, drawing pad, microphone, camera, etc.

In some embodiments, the present invention can include speech recognition software that converts speech input into cues, instructions, or feedback that is to be relayed to the patient. Further, the present invention can include image recognition software that enables the automatic identification and tracking of supplies and other elements captured by the patient's AR headset during the training session. With image recognition software, the present invention can identify and visually highlight the different medical supplies present in the patient's environment. For example, the healthcare provider can see the medical supplies highlighted in different colors. In addition, the image recognition software enables the present invention to gather information regarding the medication being delivered during the medical procedure by the patient. For example, the present invention can track the amount of medication being drawn up into a needle using included hardware on the AR headset. With the image recognition software, the present invention can further generate and overlay 3-Dimensional (3D) injection sites on the patient's body for the medical procedure. For example, a visual indicator such as an "X" graphic can be displayed on the patient's AR headset display, over the injection site. In addition, with the image recognition software, the present invention can provide real-time visual feedback to the healthcare provider to track the progress of the medical procedure. For example, the "X" graphic can be highlighted red when the patient is not in the correct spot, or the "X" can be highlighted green when the patient is over the correct injection site. In addition, hue analysis can be performed post-treatment for the healthcare provider to evaluate the outcome of the medical procedure remotely. Furthermore, with the image recognition software, the present invention can help alleviate different conditions that may prevent the patient from successfully performing the medical procedure. For example, the present invention can help alleviate the patient's Trypanophobia by overlaying comforting visuals such as flowers over the needle to keep the patient calm while performing the injection. The present invention can also overlay visual elements to properly project needle trajectory to the site of the injection.

In some embodiments, the present invention can incorporate other medical devices that further enable the monitoring of different variables during the medical procedure performed by the patient. For example, the AR headset can be further equipped with different health monitoring devices to help the healthcare provider track different vital signs of the patient during the medical procedure. In addition, the AR headset can be connected to external medical devices such as smart needles, or an auto-injector filled with Epinephrine. These devices are attached to the patient so that the healthcare provider can remotely deliver a dosage if the patient's vitals start indicating an allergic reaction. Further, the AR headset can incorporate Infrared (IR) technology to enable the patient to more easily locate the vein systems to perform the injection. Additional medical technologies and devices can be further implemented to increase the safety and efficacy of the training session using the present invention.

DETAILED DESCRIPTION OF THE INVENTION

Figure 1:
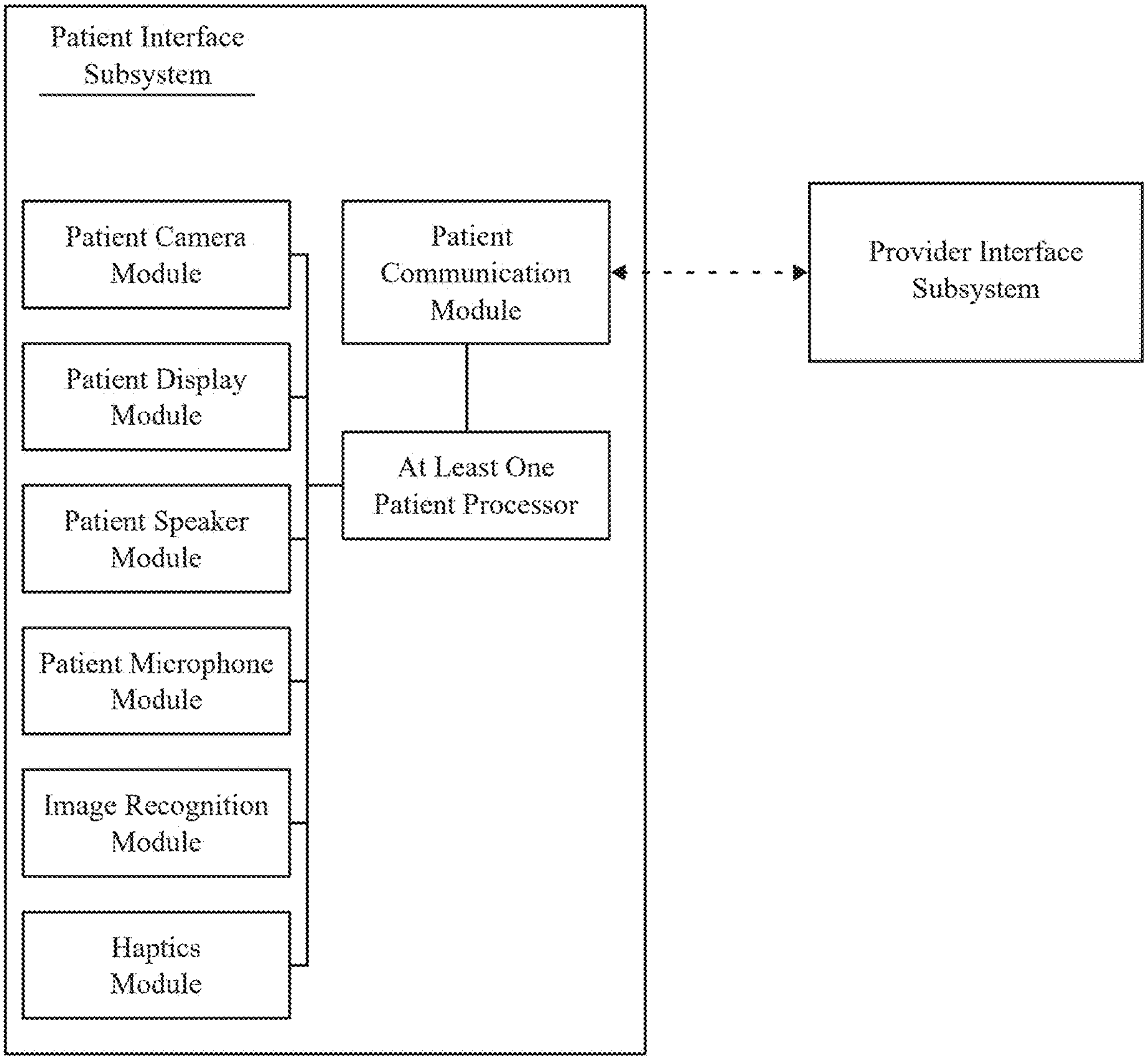
FIG. 1 is a diagram showing an overall patient interface subsystem of the present invention.
Figure 2:
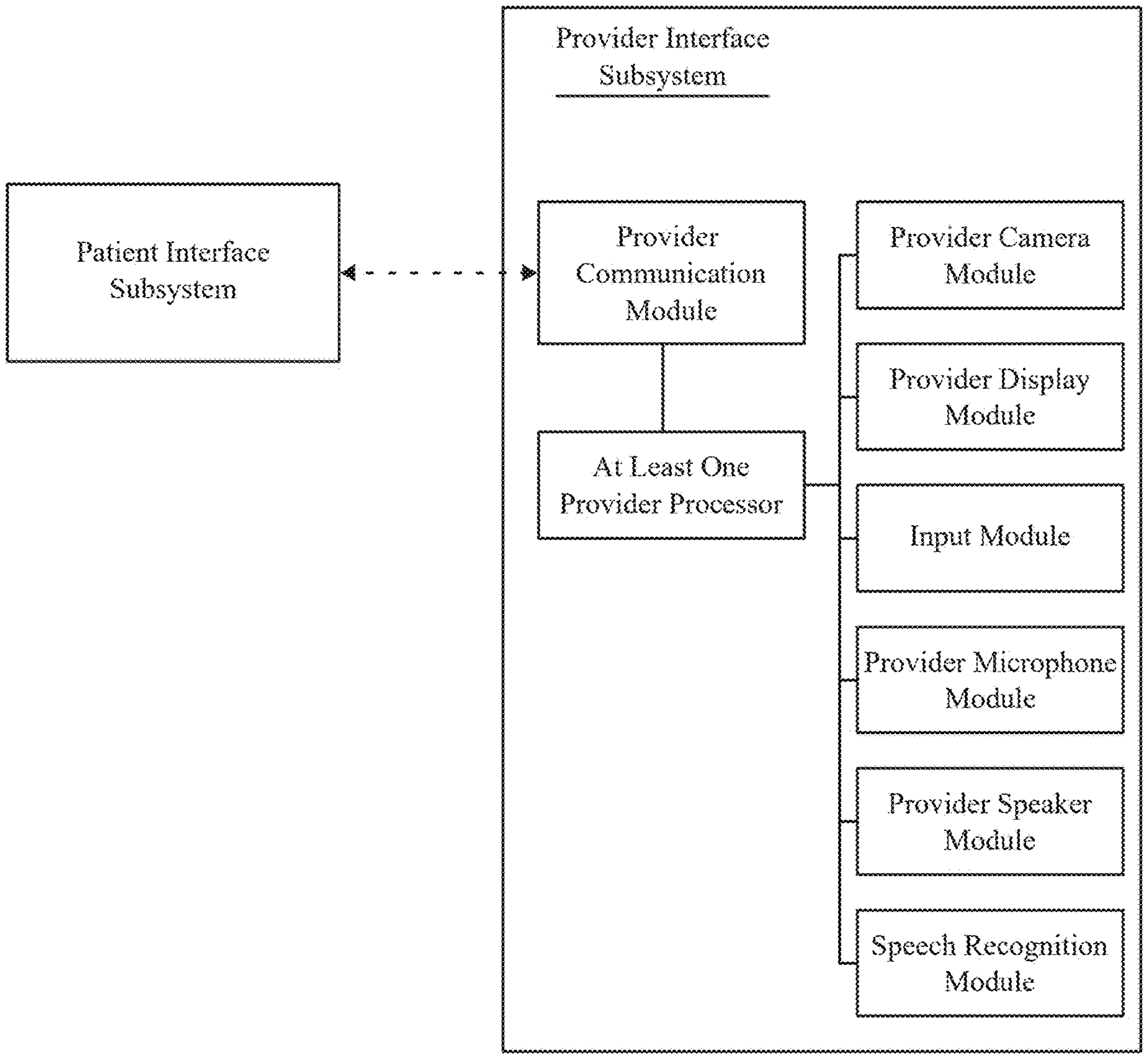
FIG. 2 is a diagram showing an overall provider interface subsystem of the present invention.
Figure 3:
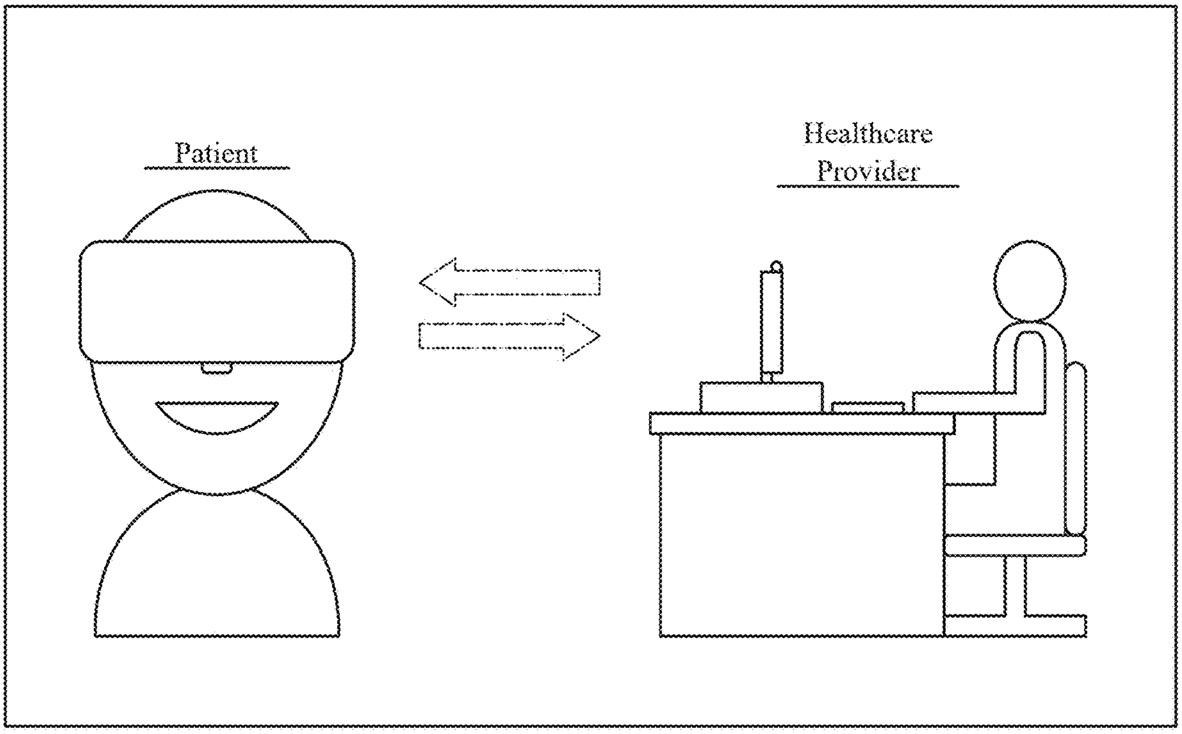
FIG. 3 is a schematic view illustrating the remote continuous communication between the patient interface subsystem and the provider interface subsystem of the present invention during a training session.

All illustrations of the drawings are for the purpose of describing selected versions of the present invention and are not intended to limit the scope of the present invention.

The present invention discloses a system for remote guidance of medical procedures that enables patients to be remotely trained by a healthcare provider to perform a medical procedure. As can be seen in FIGS. 1 through 5, the system of the present invention includes a patient interface subsystem, a patient communication module, and a patient processor. The patient interface subsystem preferably corresponds to a wearable device associated with a patient that allows for interactive wireless communication between the patient and the healthcare provider during the training procedure. The wearable device is preferably an Augmented Reality (AR) headset; however, other wearable devices with different Extended Reality (XR) technologies can be utilized. In addition, the system of the present invention further includes a patient communication module that enables communication between the patient interface subsystem and a provider interface subsystem using different communication technologies including, but not limited to, wireless communication and networking technology such as Wi-Fi. The provider interface subsystem preferably corresponds to the computing system that allows the healthcare provider to communicate in real-time with the patient using the patient interface subsystem. For example, the provider interface subsystem can include a desktop computer that allows the healthcare provider to remotely monitor the patient's actions during the procedure and provide the necessary instructions/feedback to the patient during the training session. Further, the patient processor is operatively coupled to the patient interface subsystem and the patient communication module to process the data collected by the patient interface subsystem and the data received via the patient communication module. In addition, the patient processor performs the different functions and commands received via the patient communication module.

As can be seen in FIGS. 1 through 5, the patient interface subsystem can include, but is not limited to, a patient camera module, a patient display module, a patient microphone module, a patient speaker module, and an image recognition module. The patient camera module allows for the capture of a video feed corresponding to the patient's environment and the objects present in the environment. The video feed is processed with the patient processor to apply several graphical overlays according to predetermined functions as well as instructions from the healthcare provider. The patient display module outputs the graphical overlays applied by the patient processor in an AR format. The speaker module outputs auditory cues relayed to the patient interface subsystem from the healthcare provider. The microphone module captures patient auditory data which is relayed to the healthcare provider to allow the patient and the healthcare provider to communicate to each other during the training session. Further, the image recognition module allows the processor to automatically recognize and track different elements from the video feed captured by the patient camera module during the training session.

The system of the present invention enables patients to receive training from healthcare providers so that patients can continue to perform the medical procedure in a safe and efficient manner. As can be seen in FIGS. 6 through 9, a patient interface process of the patient interface subsystem begins by authenticating the patient interface subsystem by validating a set of patient credentials of the patient. The authentication subprocess includes, but is not limited to, verifying that the patient wearing the patient interface subsystem has the permissions necessary to participate in the patient training. Once the patient interface subsystem has been authenticated and the connection has been established with the provider interface subsystem, camera data is captured with the patient camera module. The camera data is preferably a video feed that includes scene information for an environment external to the patient. In other words, the scene information can include, but is not limited to, furniture, medical supplies, other people, etc. Next, the captured camera data is evaluated with the image recognition module to confirm that a preselected set of medical supplies are present in the external environment to perform an injection. The image recognition module can implement Artificial Intelligence/Machine Learning (AI/ML) to process the captured camera data for automatic identification of medical supplies that are present in the patient's environment. The healthcare provider or the patient interface subsystem can alert the patient via the patient interface subsystem of any missing medical supplies and instruct the patient to obtain the missing medical supplies before the injection.

In addition, the camera data can be simultaneously transmitted to the provider interface subsystem via the patient communication module so that the healthcare provider can monitor the patient in real time, as can be seen in FIGS. 6 through 9. Further, provider instructions can be received from the provider interface subsystem via the patient communication module. The provider instructions include guidance or feedback from the healthcare provider that help train the patient on performing the medical procedure. Further, one or more visual cues are generated in response to the received provider instructions. The visual cues can be graphical representations of the provider instructions to give the patient visual aids while performing the medical procedure. The visual cues can be selected from a cue set consisting of a needle position cue, an injection overlay cue, and a site map cue. Next, a first graphic overlay is displayed with the patient AR display module which includes the generated visual cues. Further, the camera data is continuously evaluated with the image recognition module to keep track of the location of at least one medical supply of the preselected set of medical supplies during the training session. For example, the location and position of a syringe on the patient's external environment can be tracked during the training session to ensure that the patient is appropriately handling the syringe.

In the preferred embodiment, the system of the present invention is configured to enable the remote training of a patient on how to self-deliver an injection. To do so, the image recognition module and the patient processor can be configured to track and monitor specific variables corresponding to performing an injection. The patient processor is further configured to evaluate the camera data using the image recognition module to determine whether a correct amount of medicine is present in a syringe for the injection. Certain medicine can be prepackaged inside a syringe, so verifying that the correct amount of medicine is provided in the syringe is important. In other embodiments, the patient may have to retrieve medicine from a medicine container with the syringe. The patient processor is further configured to evaluate the camera data with the image recognition module to determine whether a correct amount of medicine is drawn with a syringe from a medicine container for the injection. In other embodiments, the system of the present invention can be configured to evaluate other medical supplies that are needed for different medical procedures.

Figure 10:
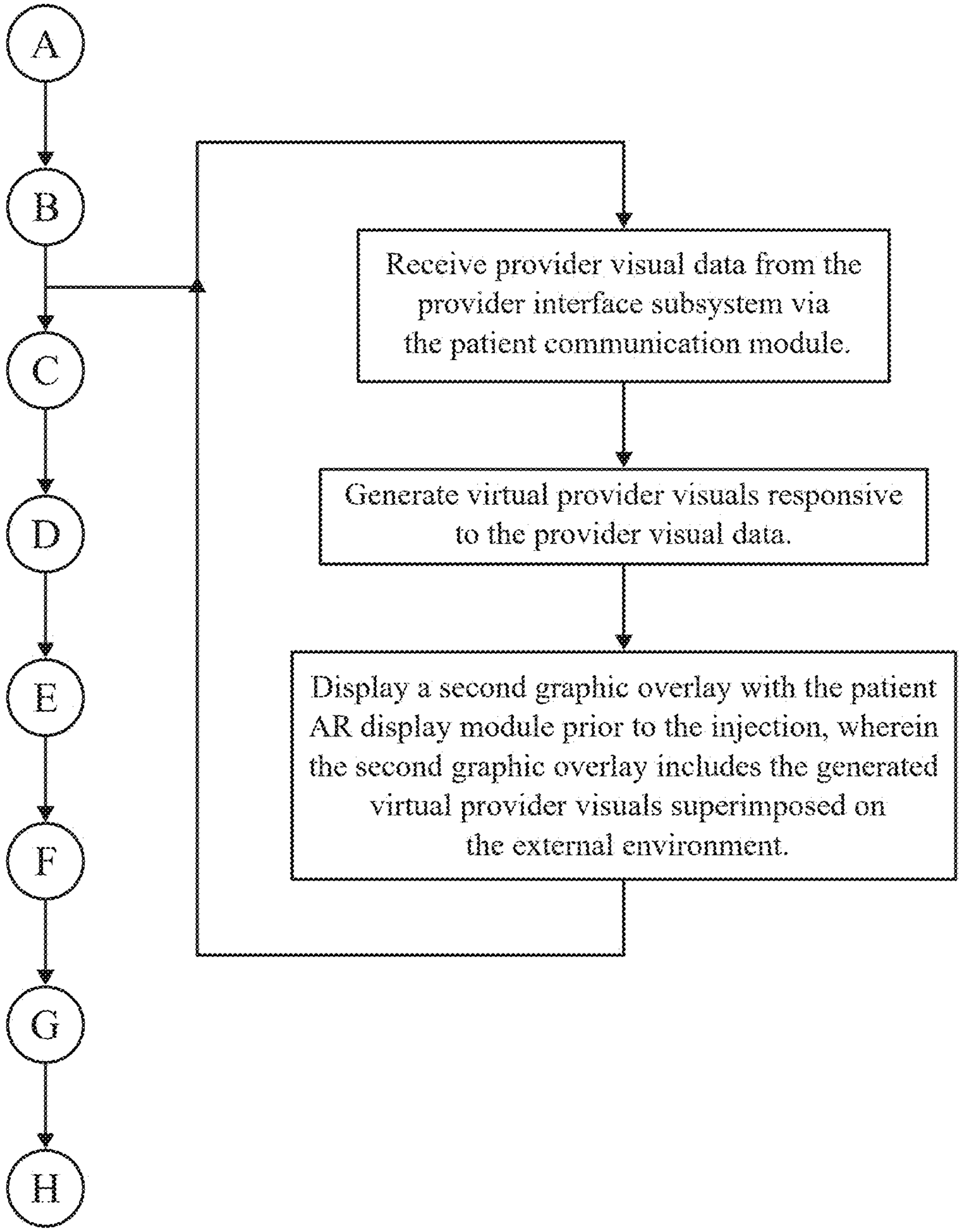
FIG. 10 is a flowchart showing the subprocess of displaying a virtual representation of the healthcare provider with the patient interface subsystem.

With the AR capabilities of the system of the present invention, various visual elements can be presented to the patient during the training session to provide confidence to the patient during the session. In some embodiments, the patient interface subsystem can provide the patient with a virtual representation of the healthcare provider. As can be seen in FIG. 10, the patient processor receives provider visual data from the provider interface subsystem via the patient communication module. Next, virtual provider visuals responsive to the provider visual data are generated. The virtual provider visuals can be, but are not limited to, a video feed of the healthcare provider, an image of the healthcare provider, or a virtual avatar of the healthcare provider. Then, a second graphic overlay is displayed with the patient AR display module prior to the injection which includes the generated virtual provider visuals superimposed on the external environment. Further, the second graphic overlay can include other visual elements to help guide the patient during the training session. The second graphic overlay may further include virtual indicia for pre-injection preparation that helps the patient get prepared for the injection. For example, the pre-injection indicia can include instructions displayed with the patient display module for the patient to follow when preparing the medical supplies during the training session. In other embodiments, the second graphic overlay may include other graphical views that help the patient perform specific tasks during the training session.

The image recognition module can help the evaluation of the camera data to determine different variables that need to be monitored during the training session. The patient interface subsystem can store a predetermined list of medical supplies and the corresponding supply attributes necessary for the image recognition module to identify the medical supplies in the camera data. Furthermore, the medical supplies being identified by the image recognition software preferably correspond to medical supplies needed for a medical injection. The preselected set of medical supplies can include, but is not limited to, at least one unit of: an auto-injectable epinephrine device, an auto-injectable epinephrine device clasp, a syringe disposal device, or an injection hygiene supply. In other embodiments, different medical supplies can be tracked and identified by the image recognition module for different medical procedures.

Figure 11:
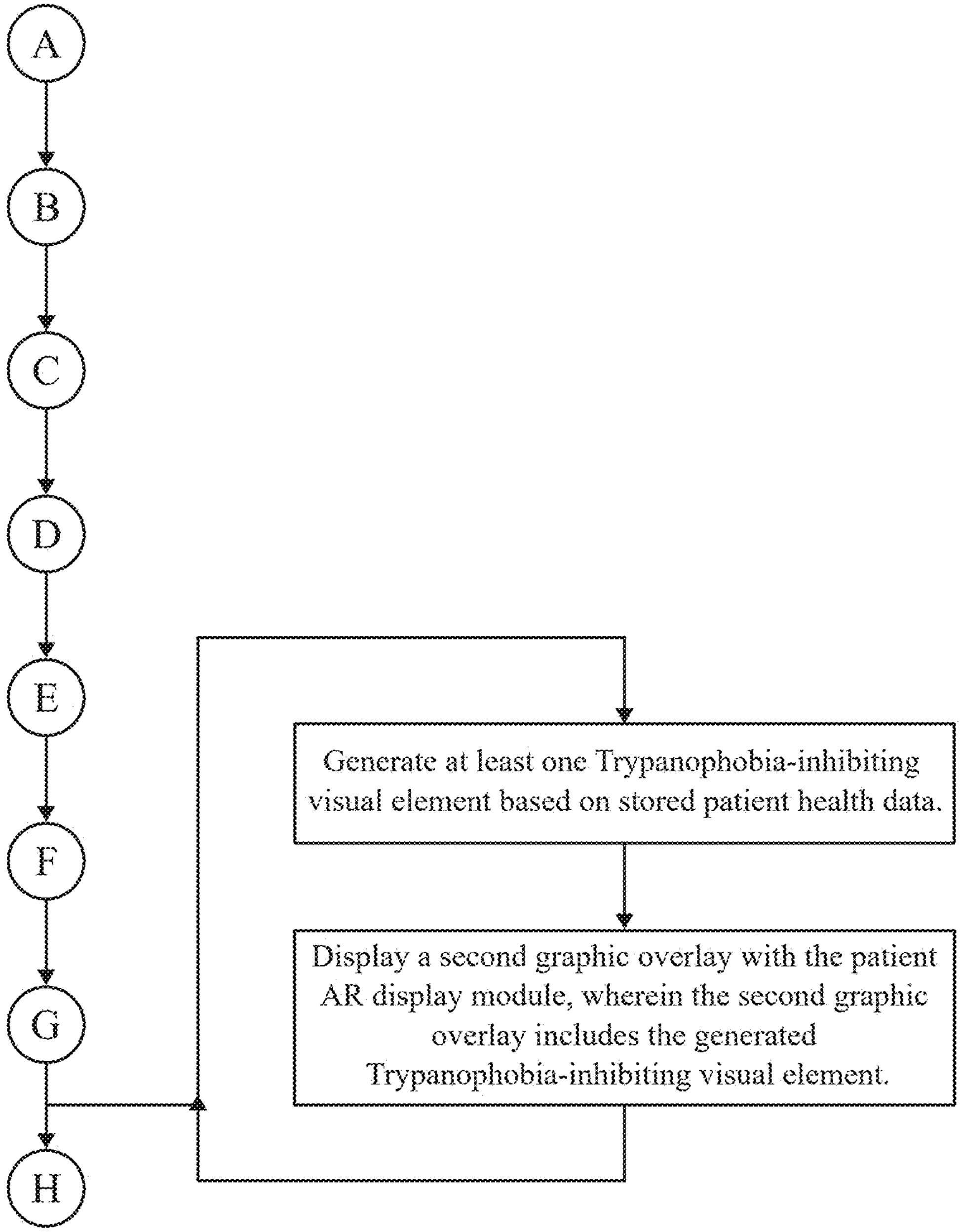
FIG. 11 is a flowchart showing the subprocess of displaying a Trypanophobia-inhibiting visual element with the patient interface subsystem.

As previously discussed, the present invention aims to facilitate the remote training of the patient so that the patient can continue to perform a medical procedure in a safe and efficient manner without direct supervision. In some embodiments, the patient processor is further configured to generate at least one Trypanophobia-inhibiting visual element, as can be seen in FIG. 11. The Trypanophobia-inhibiting visual element is configured to help the patient overcome the patient's fear of needles. For example, the Trypanophobia-inhibiting visual element can be flowers or other comforting visuals that alleviate the patient's fear of needles. The generation Trypanophobia-inhibiting visual element can be based on stored patient health data. In other words, the patient interface subsystem can automatically generate the Trypanophobia-inhibiting visual element if the patient's health records indicate that the patient has a fear of needles. Next, the second graphic overlay is displayed with the patient AR display module which also includes the generated Trypanophobia-inhibiting visual element.

Figure 12:
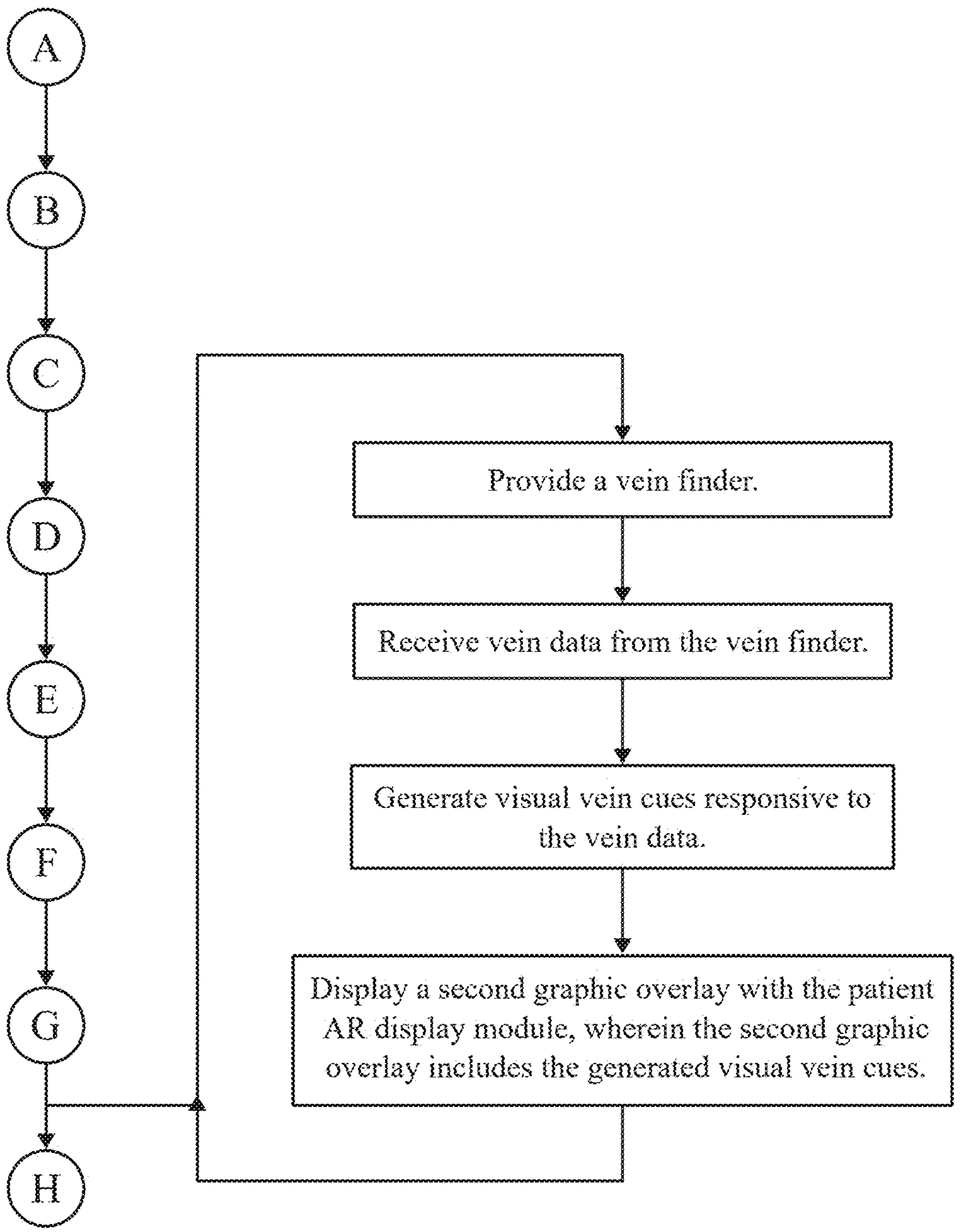
FIG. 12 is a flowchart showing the subprocess of implementing a vein finder in the patient interface subsystem of the present invention.

To further facilitate the safe and efficient training of the patient, the patient interface subsystem can include various medical devices that assist the patient to perform the medical procedure and enable the healthcare provider to monitor the patient's vitals. In some embodiments, the system of the present invention may further comprise a vein finder that is operatively coupled to the patient interface subsystem to help the patient locate the necessary veins to perform the injection, as can be seen in FIG. 12. The patient processor receives vein data from the vein finder which is used to generate visual vein cues responsive to the vein data. For example, the visual vein cues can be a graphical highlight on the body area or a graphical element pointing to the location of the veins. Further, the second graphic overlay is displayed with the patient AR display module which includes the generated visual vein cues.

Figure 13:
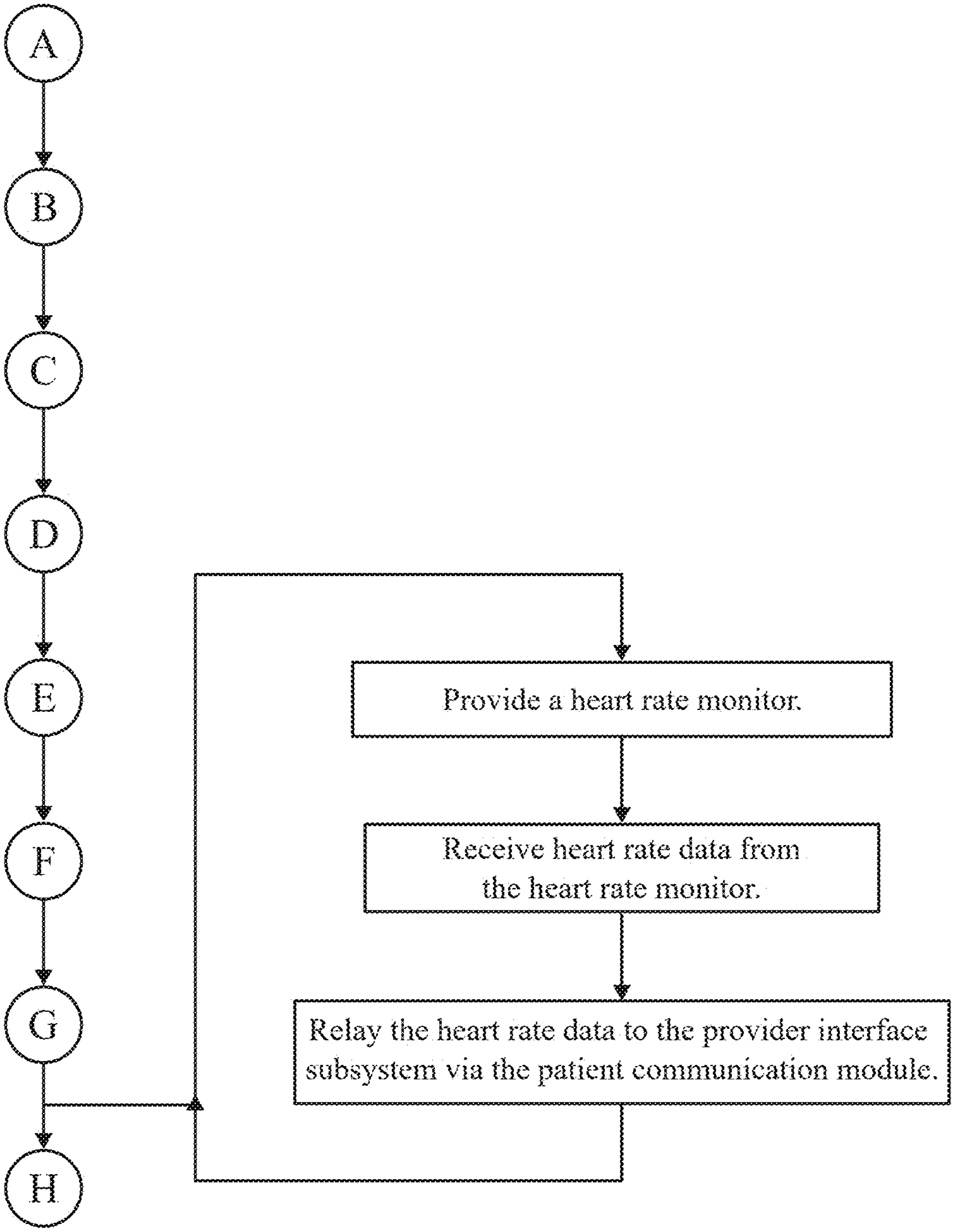
FIG. 13 is a flowchart showing the subprocess of implementing a heart rate monitor in the patient interface subsystem of the present invention, wherein the heart rate monitor is used to generate heart rate data of the patient that is relayed to the provider interface subsystem during the training session.

Further, the system of the present invention can include monitoring devices that enable the tracking of different patient's health vitals during the training session. In some embodiments, the system of the present invention may further comprise a heart rate monitor that is operatively coupled to the patient interface subsystem to help the healthcare provider to monitor the patient's heart rate during the training session, as can be seen in FIG. 13. At least one patient processor is further configured to receive heart rate data from the heart rate monitor which corresponds to the patient's heart rate. In addition, the heart rate data can be relayed to the provider interface subsystem via the patient communication module so that the healthcare provider can also monitor the patient's heart rate.

Figure 14:
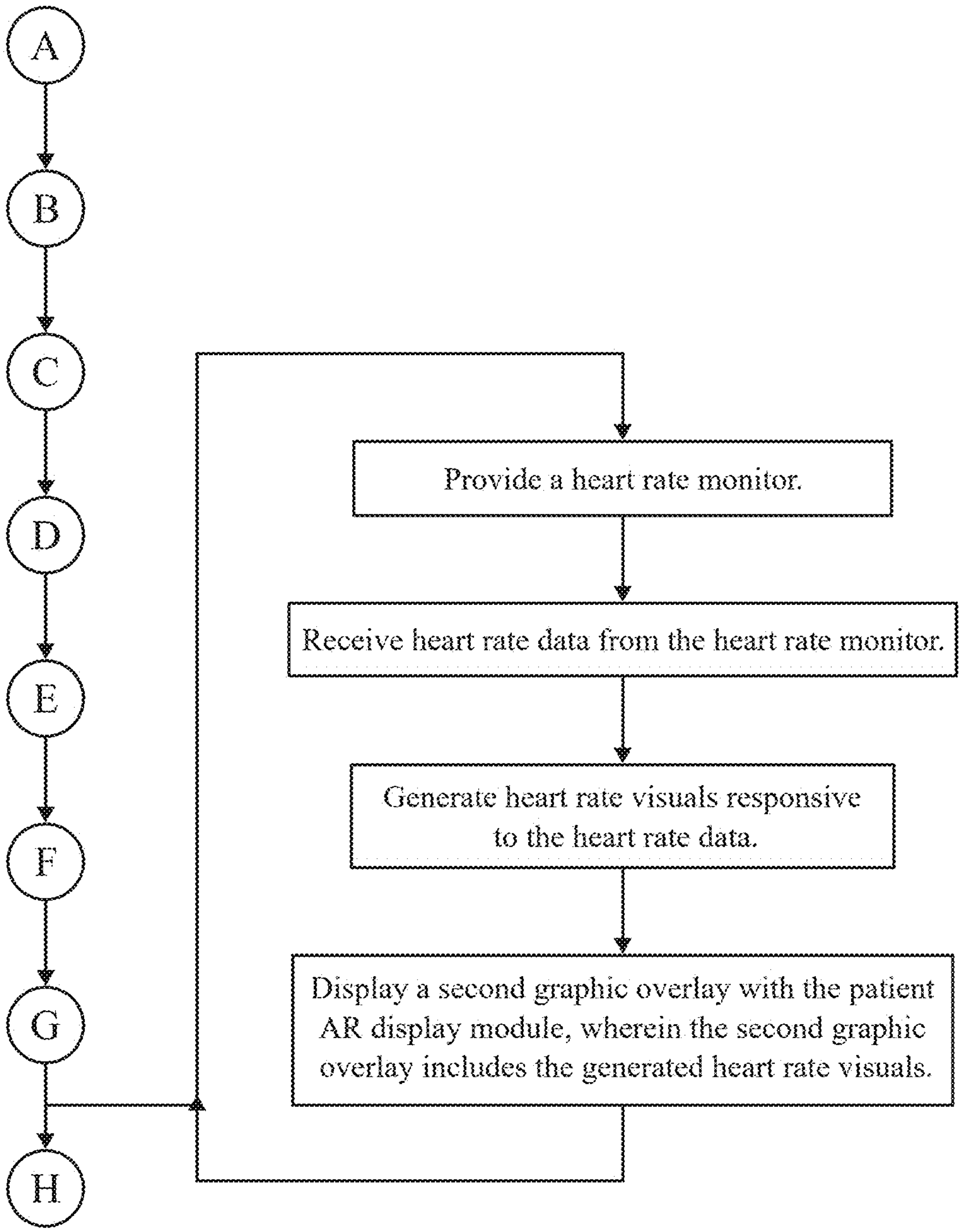
FIG. 14 is a flowchart showing the subprocess of implementing the heart rate monitor in the patient interface subsystem of the present invention, wherein the heart rate data of the patient is sent back to the provider via the patient communication module.

In addition to providing the healthcare provider with the patient's heart rate, the patient can also monitor their heart rate via the patient interface subsystem. As can be seen in FIG. 14, the patient processor can receive the heart rate data from the heart rate monitor and generate heart rate visuals responsive to the heart rate data. For example, the heart rate visuals can be visual representations of the heart rate that allow the patient to clearly monitor their heart rate. Then, the second graphic overlay is displayed with the patient AR display module which includes the generated heart rate visuals. In other embodiments, different medical devices can be integrated into the patient interface subsystem to help monitor different health vitals.

Figure 15:
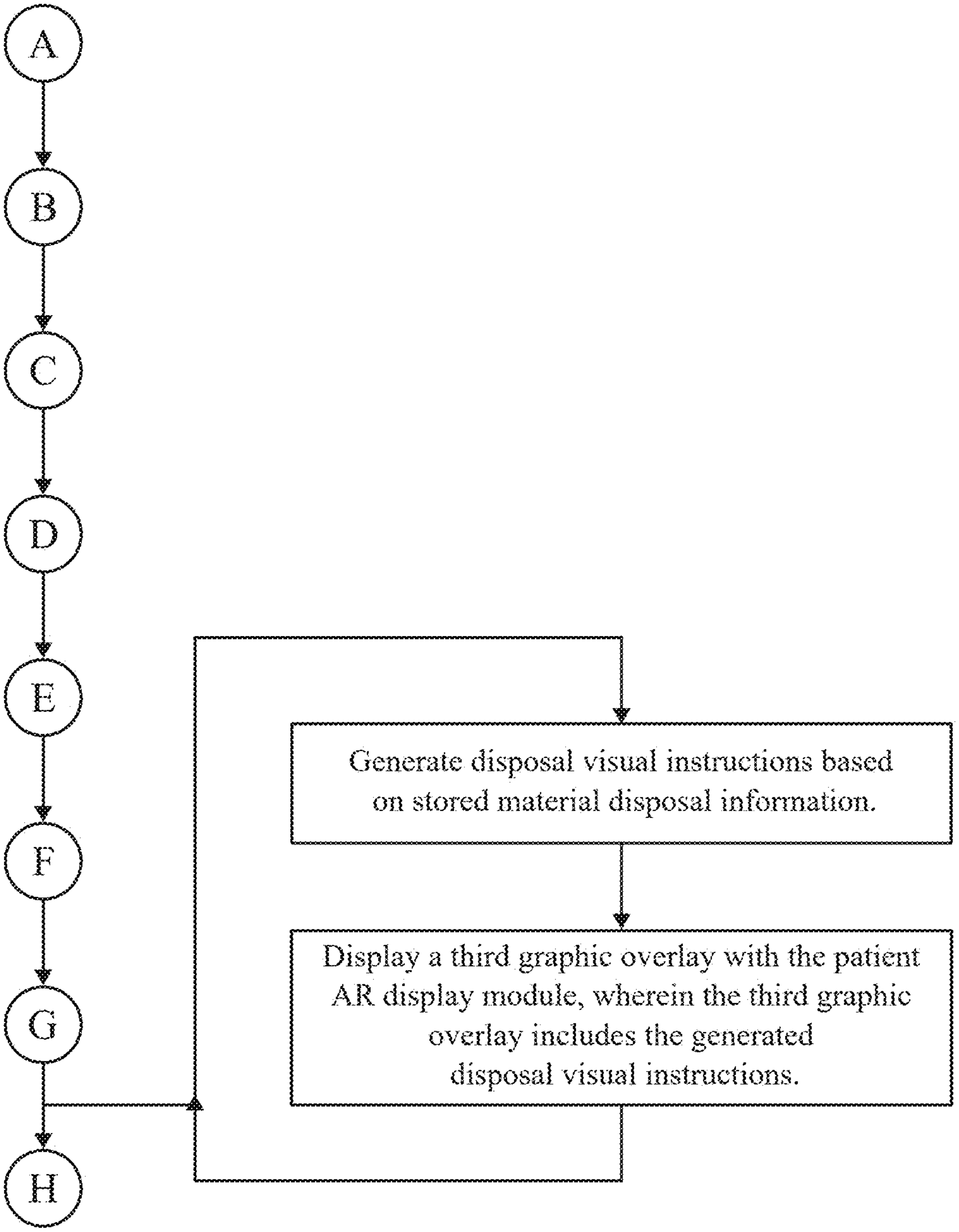
FIG. 15 is a flowchart showing the subprocess of displaying material disposal information with the patient interface subsystem of the present invention.

In some embodiments, the system of the present invention can provide means to perform post training evaluation to monitor the patient's health vitals after delivery of the medication. This way, the healthcare provider and the patient can ensure that no complications to the patient arise from the medical procedure performed. The patient processor is further configured to capture post-injection camera data with the patient camera module. The post-injection camera data is used for post-injection evaluation with the image recognition module so that the patient's body is monitored for possible physical indicators corresponding to physical reactions of the patient's body to the medicine injected. Alternatively, the post-injection camera data can be relayed to the provider interface subsystem so that the healthcare provider can perform the evaluation. In addition to post-training evaluation capabilities, the present invention can provide other functionalities for post-training tasks. In some embodiments, the patient processor can be further configured to generate disposal visual instructions based on stored material disposal information, as can be seen in FIG. 15. In other words, the patient interface subsystem can provide disposal instructions for the patient to safely dispose of the syringe and other used medical supplies. The disposal instructions can also be received from the healthcare provider. Further, a third graphic overlay is displayed with the patient AR display module which includes the generated disposal visual instructions. In other embodiments, different post-injection information can be provided to the patient via the patient interface subsystem.

Figure 16:
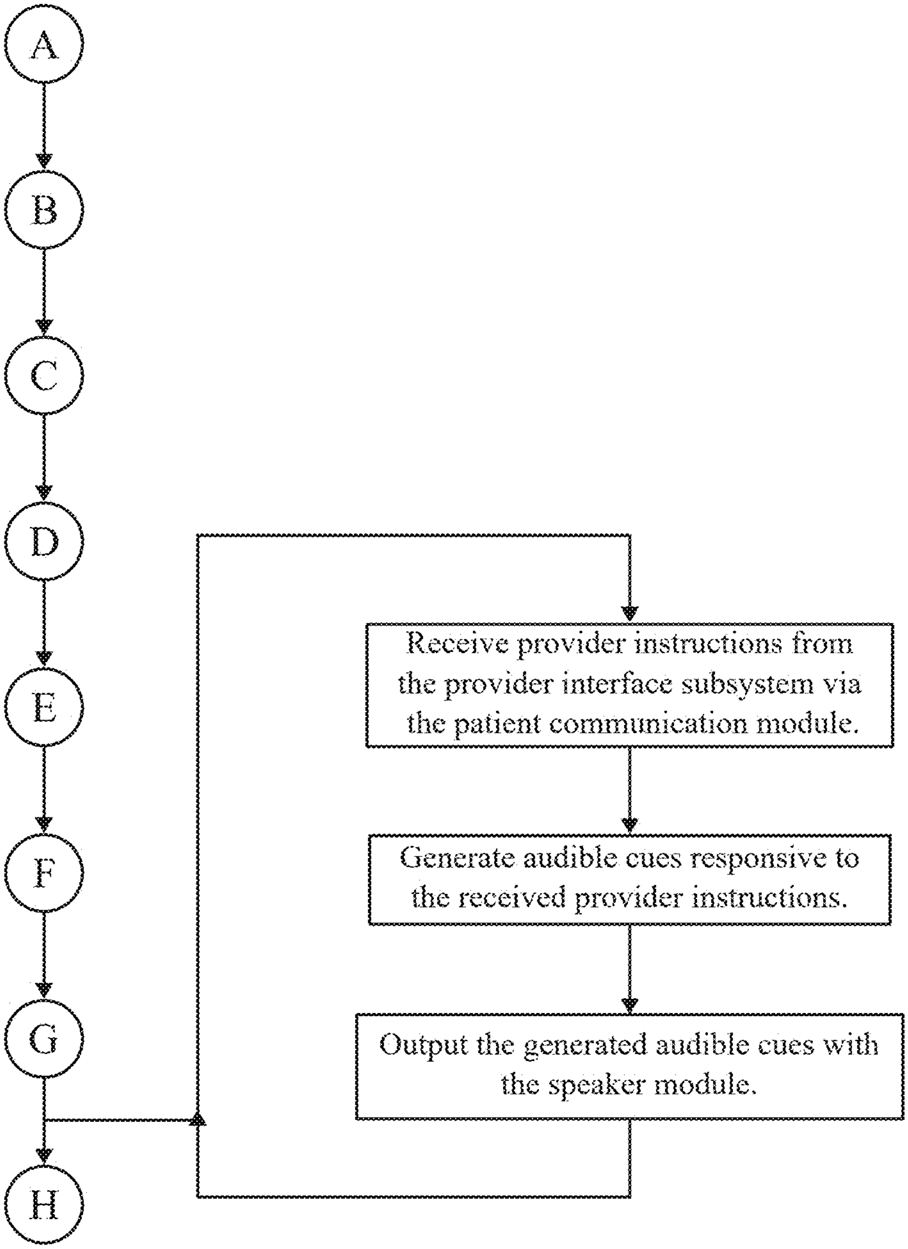
FIG. 16 is a flowchart showing the subprocess of outputting audible cues based on provider instructions with the patient interface subsystem of the present invention.

As previously discussed, the system of the present invention allows for cues and instructions to be output to the patient via the patient interface subsystem in different formats. As can be seen in FIG. 16, the patient processor can be further configured to receive provider instructions from the provider interface subsystem via the patient communication module. The provider instructions can include audible instructions to guide the patient. Next, the patient processor generates audible cues responsive to the received provider instructions, and the generated audible cues are output with the speaker module. This way, the patient can listen to the healthcare provider's guidance during the training session.

Figure 17:
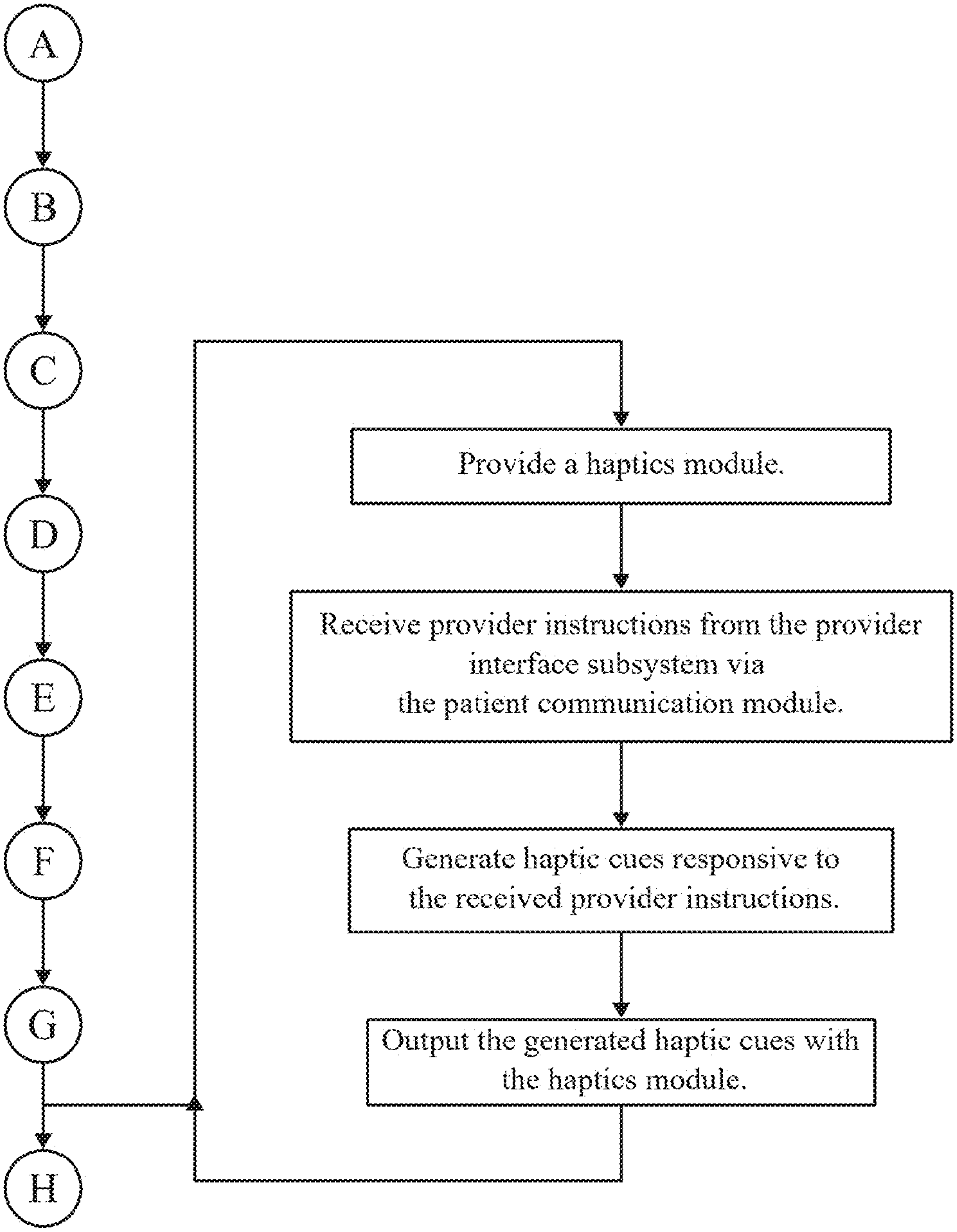
FIG. 17 is a flowchart showing the subprocess of outputting haptic cues based on provider instructions with the patient interface subsystem of the present invention.

In another embodiment, the patient instructions can be output to the patient in other forms that are not visual or auditory. For example, the patient can be signaled to perform specific tasks via physical cues to the patient. As can be seen in FIG. 17, the patient interface subsystem may further comprise a haptics module that is operatively coupled to the patient interface subsystem. The haptics module enables the output of physical cues to the patient to enhance the guidance provided by the healthcare provider during the training session. To do so, the patient processor receives provider instructions from the provider interface subsystem via the patient communication module which include physical cues to be output by the haptics module. The patient processor generates haptic cues responsive to the received provider instructions and outputs the generated haptic cues with the haptics module.

Figure 18:
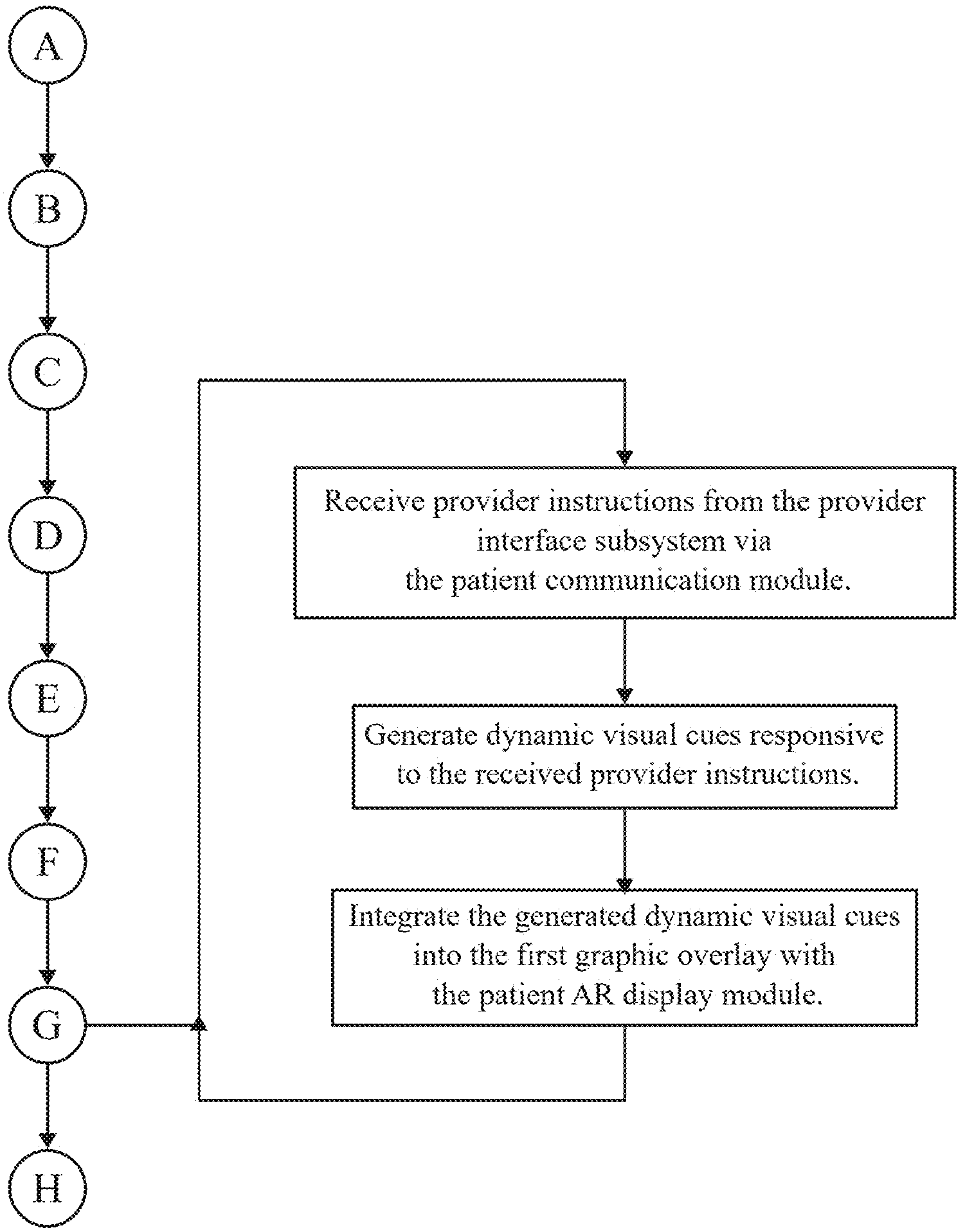
FIG. 18 is a flowchart showing the subprocess of outputting dynamic visual cues based on provider instructions with the patient interface subsystem of the present invention.

As previously discussed, the patient display module is preferably an AR display that enables the different graphic overlays, cues, and other visual elements to be superimposed on the patient's field of vision. In some embodiments, the patient processor is configured to receive provider instructions from the provider interface subsystem via the patient communication module that include dynamic visual cues that are dynamically displayed on the AR display, as can be seen in FIG. 18. The patient processor generates dynamic visual cues responsive to the received provider instructions and integrates the generated dynamic visual cues into the first graphic overlay with the patient AR display module. In other words, the visual cues are dynamically displayed so that the visual cues change position and orientation based on the patient's viewpoint. This way, the visual cues can be kept present on the patient's view during the training session.

Figure 19:
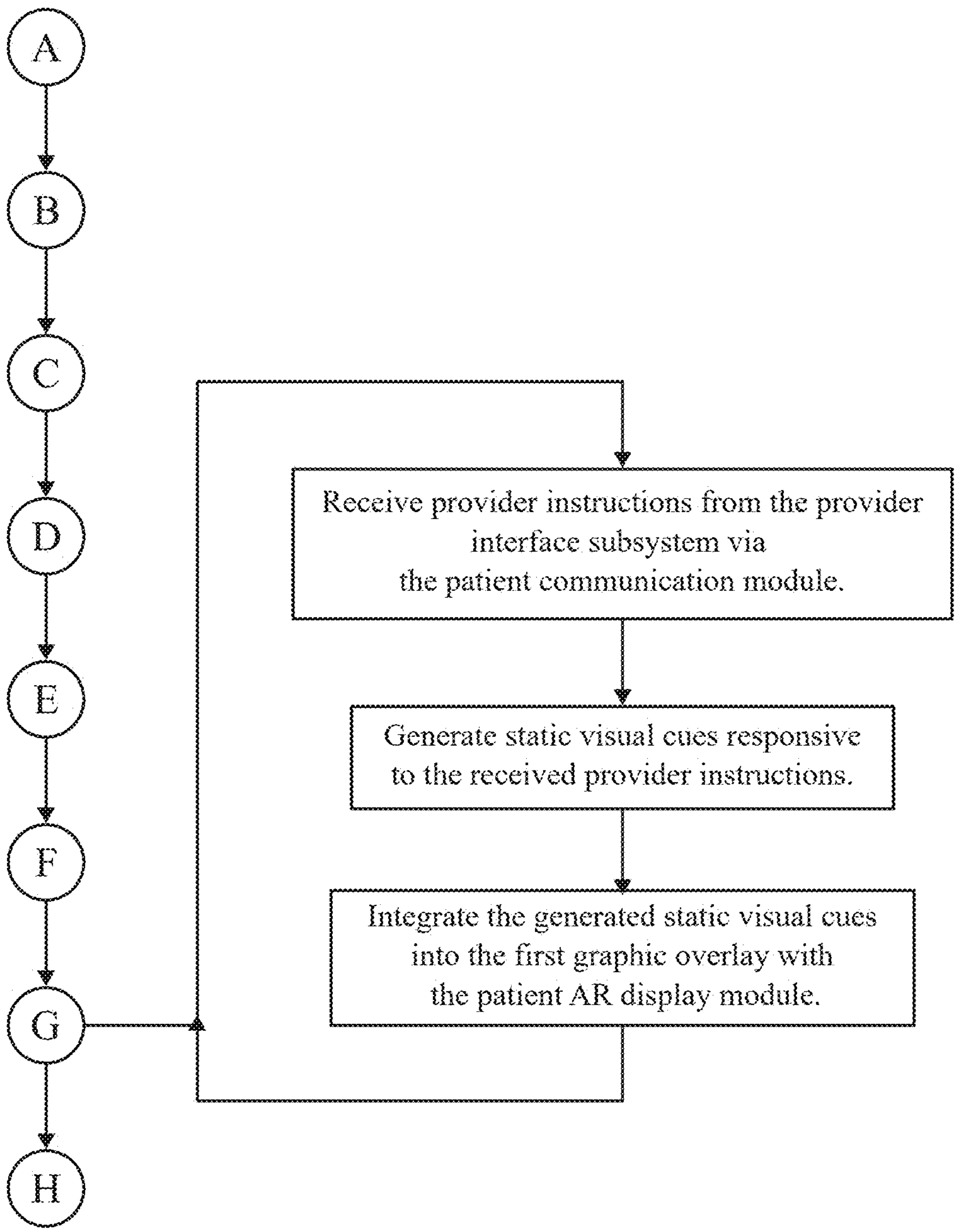
FIG. 19 is a flowchart showing the subprocess of outputting static visual cues based on provider instructions with the patient interface subsystem of the present invention.
Figure 20:
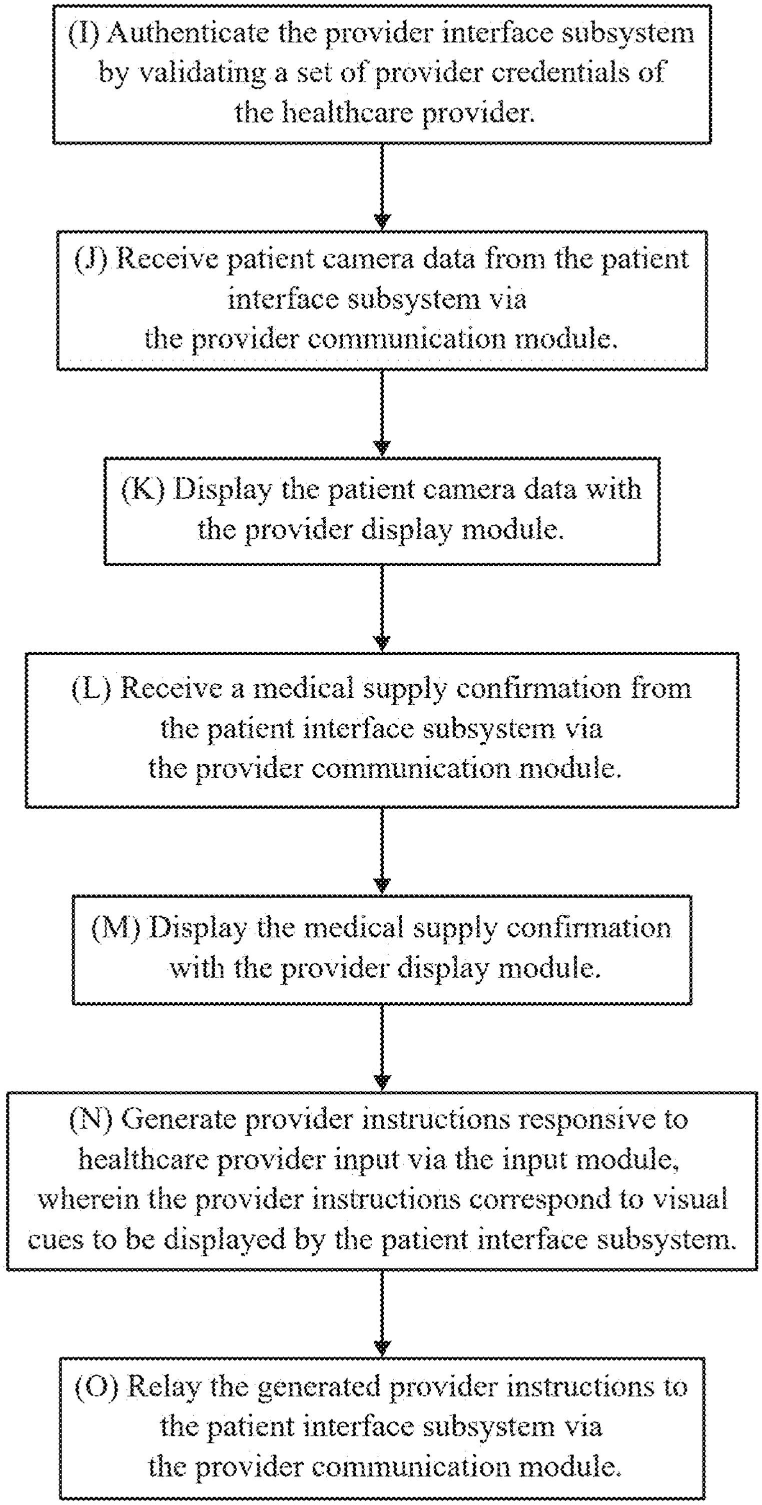
FIG. 20 is a flowchart showing the overall processes performed with the provider interface subsystem of the present invention.

In other embodiments, the at least one patient processor is configured to receive provider instructions from the provider interface subsystem via the patient communication module that include static visual cues that are statically displayed on the AR display. As can be seen in FIG. 19, the patient processor generates static visual cues responsive to the received provider instructions and integrates the generated static visual cues into the first graphic overlay with the patient AR display module. In other words, the visual cues are statically displayed so that the visual cues do not change position or orientation regardless of the patient's viewpoint. This way, the visual cues are only displayed on a predetermined location and/or orientation on the patient's environment.

In some embodiments, the generated cues corresponding to the provider instructions given during the training session can be stored for future reference by the patient. After the visual cues have been generated according to the provider instructions, the patient processor is further configured to store the generated visual cues for subsequent injections. The patient interface subsystem may be configured to have an integrated memory storage device or be configured to accommodate an external storage device that can be selectively coupled to the patient interface subsystem.

The present invention also discloses a system for remote guidance of medical procedures that enables healthcare providers to remotely train a patient to self-perform a medical procedure. As can be seen in FIGS. 1 through 5, the system of the present invention may further include a provider interface subsystem, a provider communication module, and a provider processor. The provider interface subsystem preferably corresponds to a computing system that allows for interactive wireless communication between the healthcare provider and the patient. For example, the provider interface subsystem can be a computer workstation from where the healthcare provider can monitor the patient's training session. The provider communication module enables remote real-time continuous communication between the provider interface subsystem and the patient interface subsystem during the training session. The provider processor is operatively coupled to the provider interface subsystem and the provider communication module to enable the operation of the provider interface subsystem by processing the data captured and received as well as performing the different functions that enable the remote guidance of the patient during the training session.

As can be seen in FIGS. 1 through 5, the provider interface subsystem also includes a provider camera module, a provider display module, a provider speaker module, a provider microphone module, and an input module. The provider camera module captures camera data corresponding to the healthcare provider's actions during the training session. The provider display module displays the video feed captured by the provider camera module as well as the data relayed to the provider interface subsystem from the patient interface subsystem via the provider communication module. The input module enables the healthcare provider to enter input data corresponding to cues or instructions to direct the patient during the training session. Further, the provider speaker module and the provider microphone module enable the healthcare provider to communicate with the patient during the training session. The provider microphone module also captures audible instructions from the healthcare provider.

The system of the present invention enables healthcare providers to remotely train patients to perform medical procedures without in-person supervision from the healthcare provider. As can be seen in FIGS. 6 through 8 and 20, a provider interface process begins by authenticating the provider interface subsystem by validating a set of provider credentials of the healthcare provider. The authentication subprocess includes, but is not limited to, verifying that the provider using the provider interface subsystem has the permissions necessary to participate in the patient training. Once the provider interface subsystem has been authenticated and the connection has been established with the patient interface subsystem, patient camera data is received from the patient interface subsystem via the provider communication module. The patient camera data includes scene information of an external environment of the patient that allows the healthcare provider to monitor the patient during the training session. Next, the patient camera data is displayed with the provider display module so that the healthcare provider can monitor the patient's actions during the training session. Next, a medical supply confirmation is received from the patient interface subsystem via the provider communication module. The medical supply confirmation results from an evaluation by the patient interface subsystem to confirm that a preselected set of medical supplies are present in the external environment of the patient to perform an injection. In other words, the system of the present invention provides the healthcare provider with information that assures the healthcare provider that the patient has the tools necessary to perform the medical procedure. The medical supply confirmation is also displayed with the provider display module. Next, provider instructions are generated responsive to healthcare provider input via the input module. The provider instructions preferably correspond to visual cues to be displayed by the patient interface subsystem. For example, the healthcare provider can instruct the patient interface subsystem to show the patient where to inject the medicine. Further, the generated provider instructions are relayed to the patient interface subsystem via the provider communication module. This way, the healthcare provider can provide continuous guidance to the patient during the training session.

As previously discussed, the medical supply confirmation includes different information regarding the medical supplies necessary for the medical procedure. In the preferred embodiment, the medical supply confirmation includes information regarding the medical supplies necessary for the patient to perform an injection. For example, the medical supply confirmation further includes data about the amount of the medicine present in a syringe. In addition, the visual cues output by the patient interface subsystem can include visual cues from a cue set consisting of a needle position cue, an injection overlay cue, and a site map cue. In other embodiments, different medical supplies and visual cues can be generated for different medical procedures.

Figure 4:
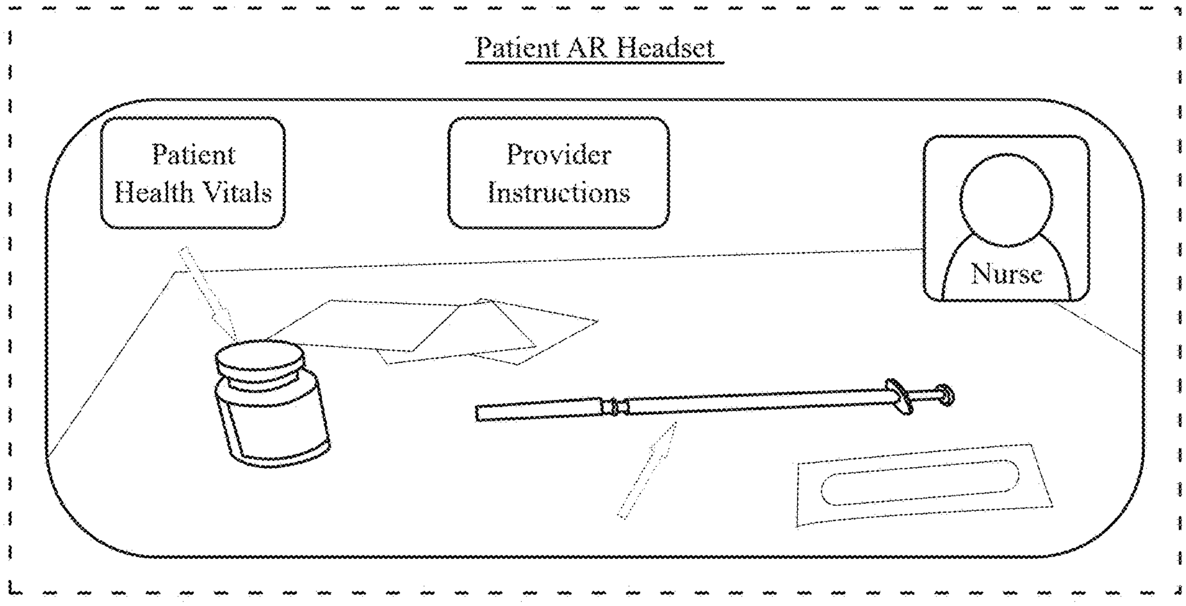
FIG. 4 is a schematic view illustrating the patient interface subsystem of the present invention.
Figure 5:
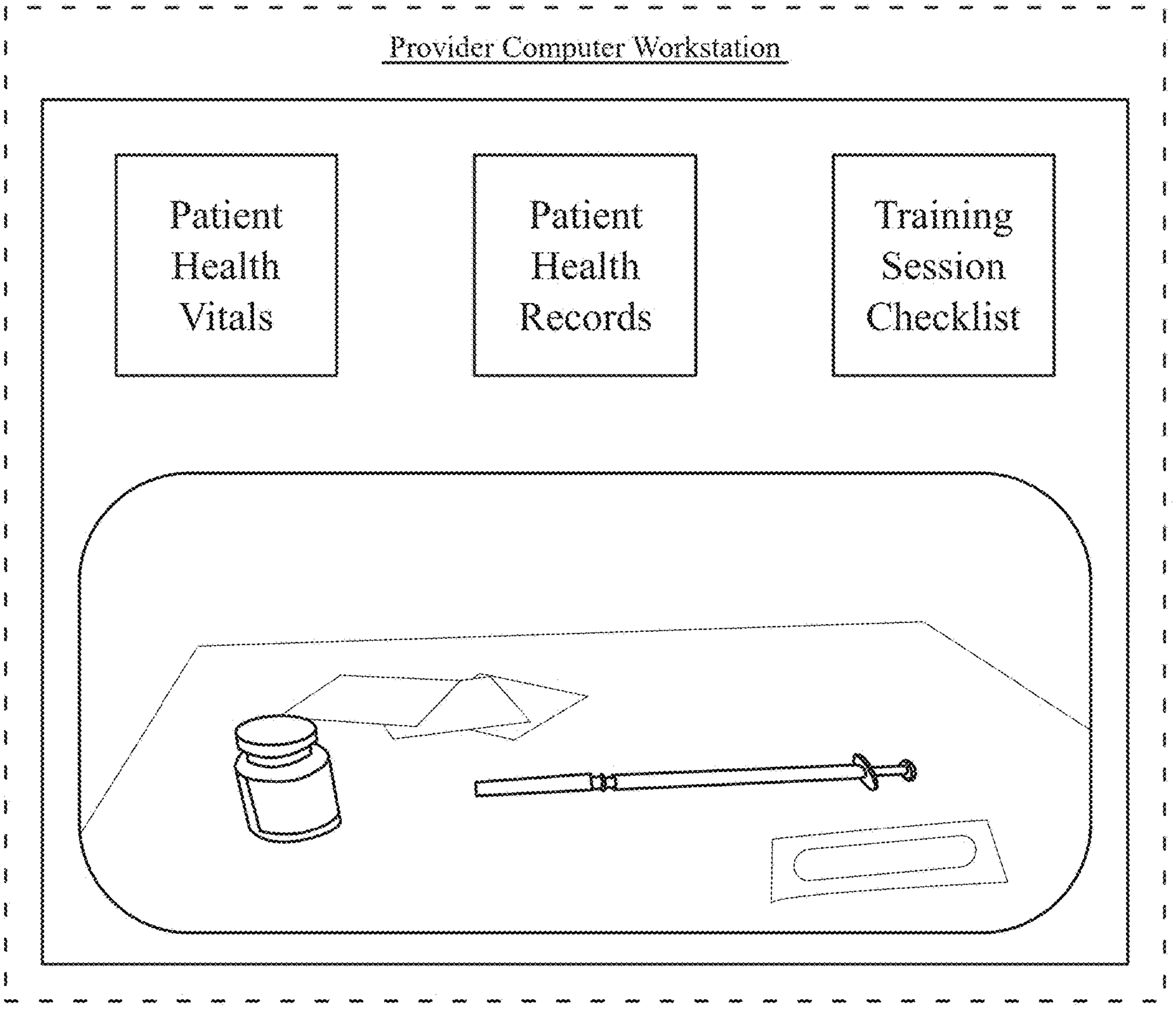
FIG. 5 is a schematic view illustrating the provider interface subsystem of the present invention.
Figure 21:
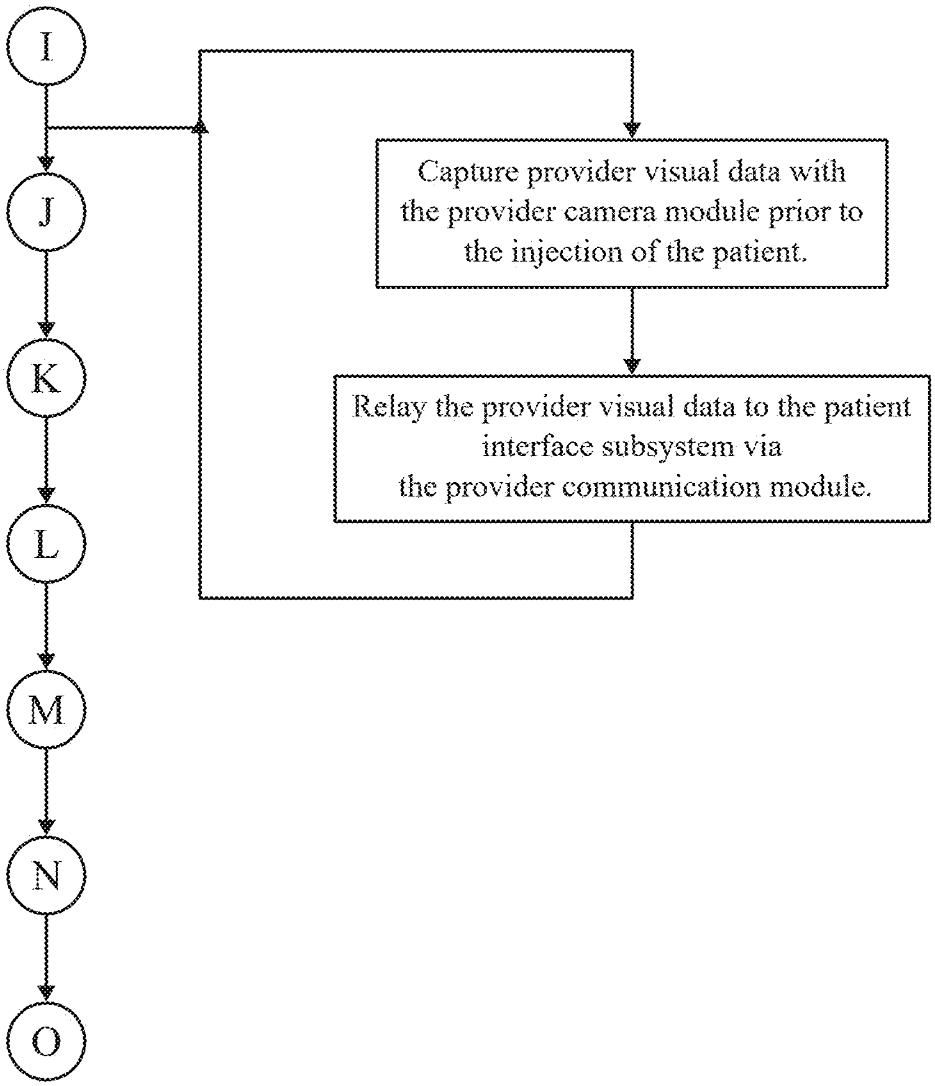
FIG. 21 is a flowchart showing the subprocess of capturing provider visual data with the provider camera module of the provider interface subsystem of the present invention.

As previously discussed, the system of the present invention can provide a graphical representation of the healthcare provider displayed to the patient on the patient interface system. As can be seen in FIGS. 4 and 21, the provider processor is further configured to capture provider visual data with the provider camera module prior to the injection of the patient. The provider visual data includes data that can be used by the patient interface subsystem to generate a visual representation of the healthcare provider. For example, the visual representation can be a video feed of the healthcare provider captured by the provider camera module, a static image of the healthcare provider, or a virtual avatar of the healthcare provider. The provider visual data is relayed to the patient interface subsystem via the provider communication module during the training session so that the provider visual data can be used by the patient interface subsystem.

As previously discussed, the provider instructions enable the healthcare provider to provide remote guidance to the patient during the training session for different tasks the patient needs to perform during the medical procedure. In some embodiments, the provider instructions can include pre-injection instructions for pre-injection preparation of the patient. The pre-injection instructions provide the patient with instructions on how to prepare for the injection. Further, the provider instructions can include injection training instructions for the patient. The injection training instructions can instruct the patient on how to perform the injection. In other embodiments, different instructions can be provided for different medical procedures.

Figure 22:
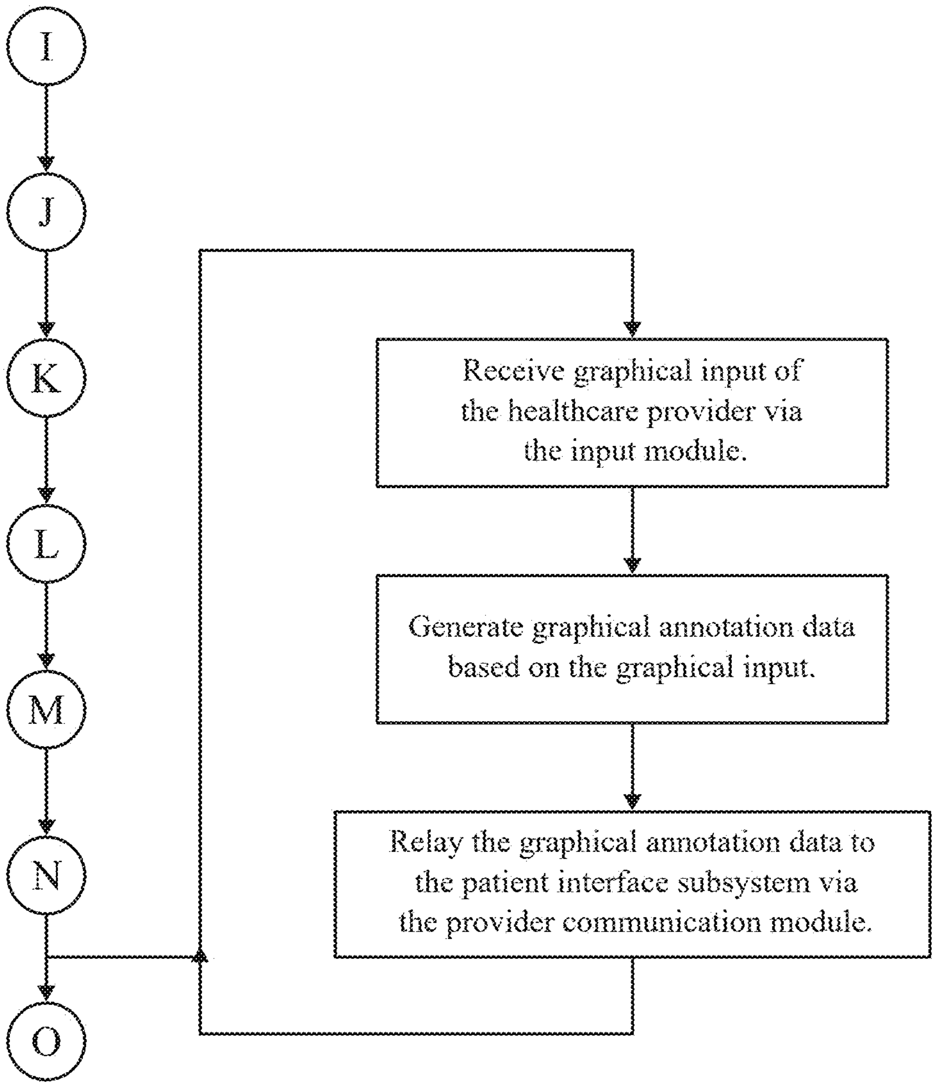
FIG. 22 is a flowchart showing the subprocess of generating graphical annotations with the provider interface subsystem of the present invention.
Figure 23:
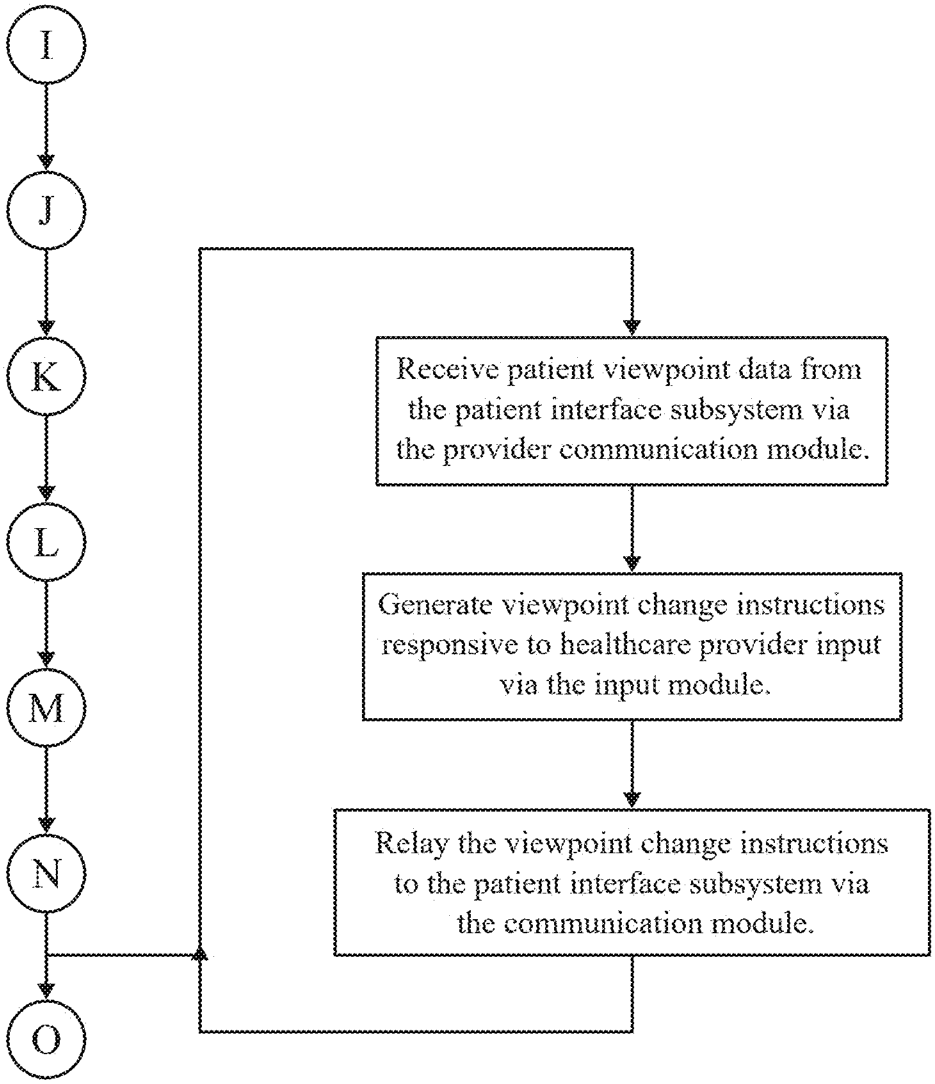
FIG. 23 is a flowchart showing the subprocess of generating patient viewpoint instructions with the provider interface subsystem of the present invention.

The input module can allow the user to input provider instructions using different media. In one embodiment, the input module can include a graphics tablet that allows the user to input graphical annotations. As can be seen in FIG. 22, the provider processor can be further configured to receive graphical input of the healthcare provider via the input module and generate graphical annotation data based on the graphical input. For example, the graphical annotations can be a visual indicator that allows the healthcare provider to visually guide the patient during the training session. The graphical annotation data is relayed to the patient interface subsystem via the provider communication module so that the patient interface subsystem can output the corresponding graphics.

In some embodiments, the viewpoint information can include viewpoint data consisting of static viewpoint data or dynamic viewpoint data. Furthermore, the viewpoint change instructions can include commands for virtual items to be pinned in the display of a patient AR display module of the patient interface subsystem. The virtual items can be pinned to maintain the virtual elements displayed at a specific location in the display of the patient interface subsystem. In other embodiments, the input module can allow for different information to be entered by the healthcare provider that is to be relayed to the patient during the training session.

Figure 24:
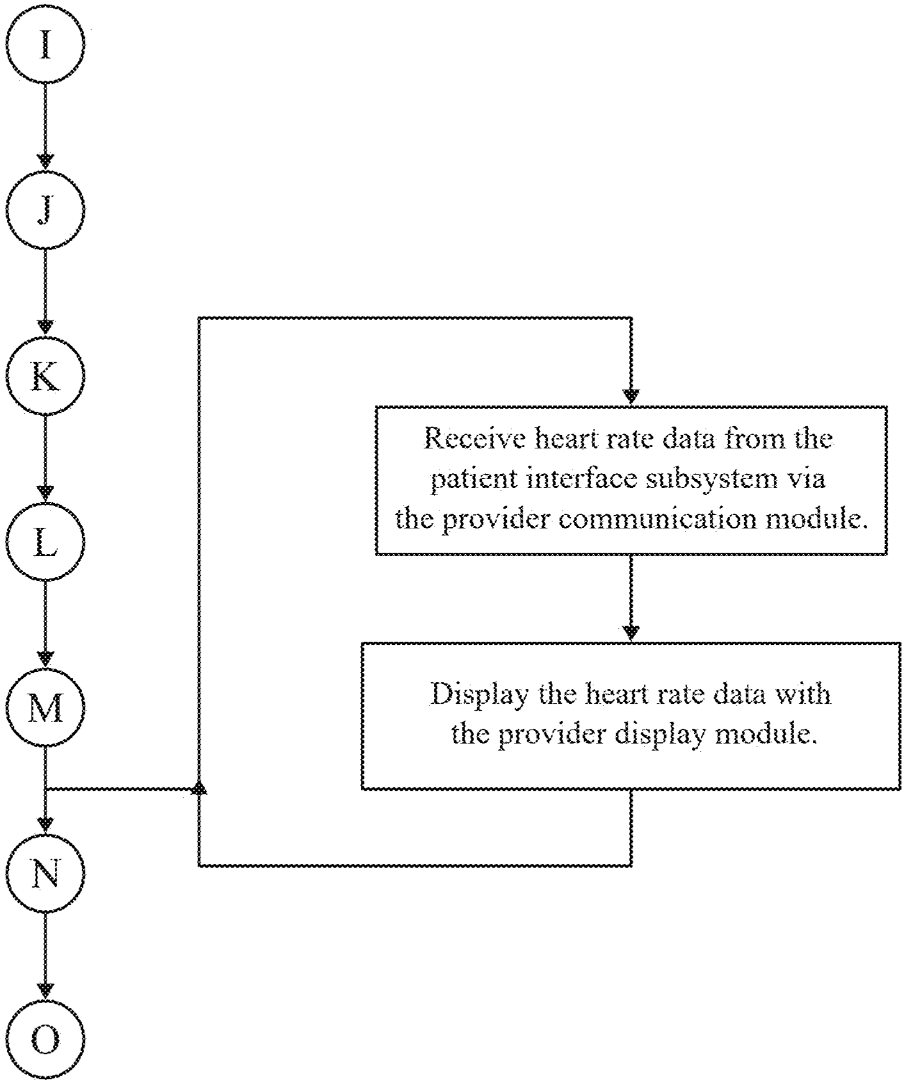
FIG. 24 is a flowchart showing the subprocess of receiving and displaying patient heart rate data with the provider interface subsystem of the present invention.

The system of the present invention enables the healthcare provider to receive patient health information to properly guide the patient during the training session. In some embodiments, the provider processor can be further configured to receive heart rate data from the patient interface subsystem via the provider communication module, as can be seen in FIG. 24. The heart rate data corresponds to the patient's heart rate during the training session that allows the healthcare provider to ensure no health complications arise from the medical procedure. Further, the heart rate data is displayed with the provider display module so that the healthcare provider can continuously monitor the patient's heart rate.

Furthermore, the system of the present invention allows healthcare providers to perform post-procedural evaluations to confirm that the procedure has been performed correctly and no adverse body reactions have occurred. The provider processor can be further configured to receive post-injection camera data from the patient interface subsystem via the provider communication module. The post-injection camera data is used for post-injection evaluation of the patient, either performed automatically by the system or manually by the healthcare provider. For example, the post-injection evaluation can include determining whether a patient body reaction to the injection occurred. In other embodiments, different post-injection evaluations can be performed by the system or the healthcare provider.

Figure 25:
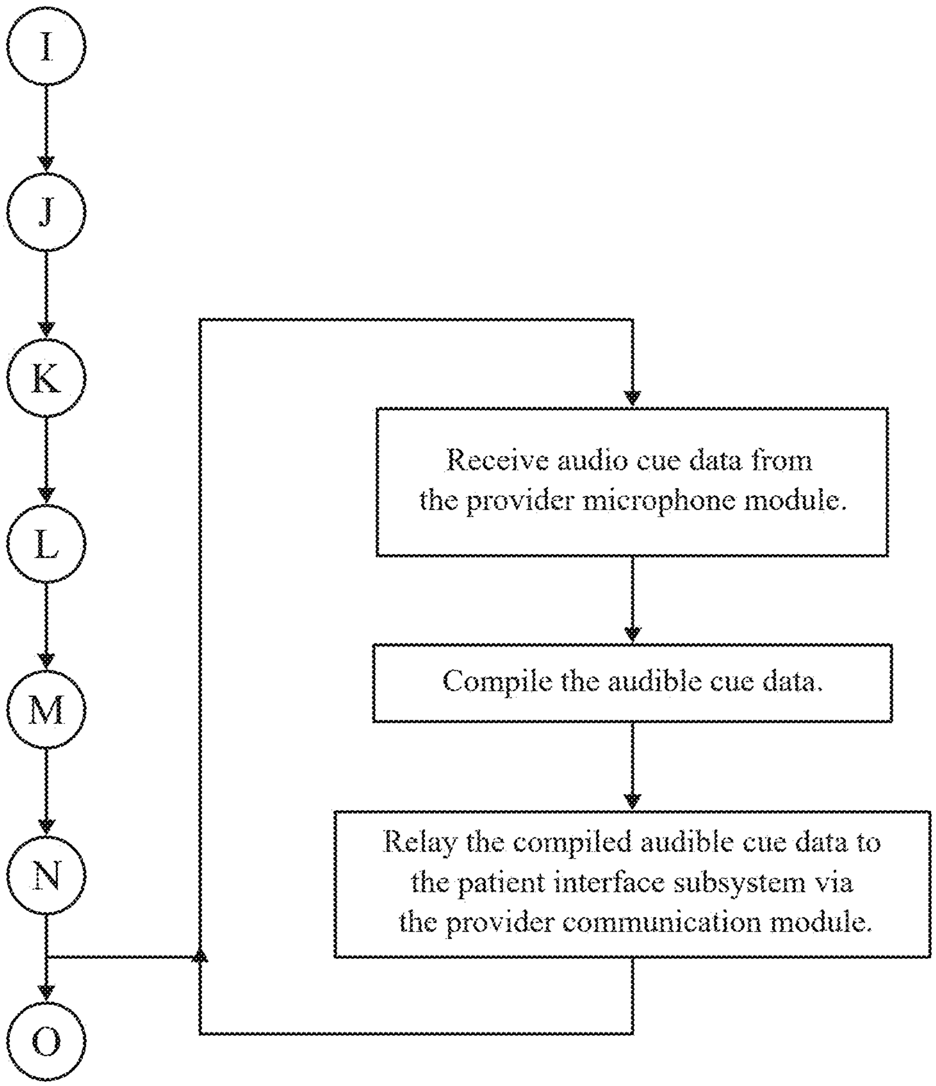
FIG. 25 is a flowchart showing the subprocess of capturing audio cue data with the provider interface subsystem of the present invention.

As previously discussed, the provider interface subsystem enables healthcare providers to transmit different cues and instructions to the patient. In some embodiments, at least one provider processor may be further configured to receive audible data which can be transmitted to the patient interface subsystem to be output as audio, as can be seen in FIG. 25. The provider processor is further configured to receive audio cue data from the provider microphone module. The audio cue data can include verbal commands spoken by the healthcare provider on the provider microphone module. Next, the provider processor compiles the audio cue data. The audible cue data preferably corresponds to audible cues to be output by the patient interface subsystem. Then, the compiled audible cue data is relayed to the patient interface subsystem via the provider communication module so that the corresponding audio is output by the patient interface subsystem to the patient during the training session.

Figure 26:
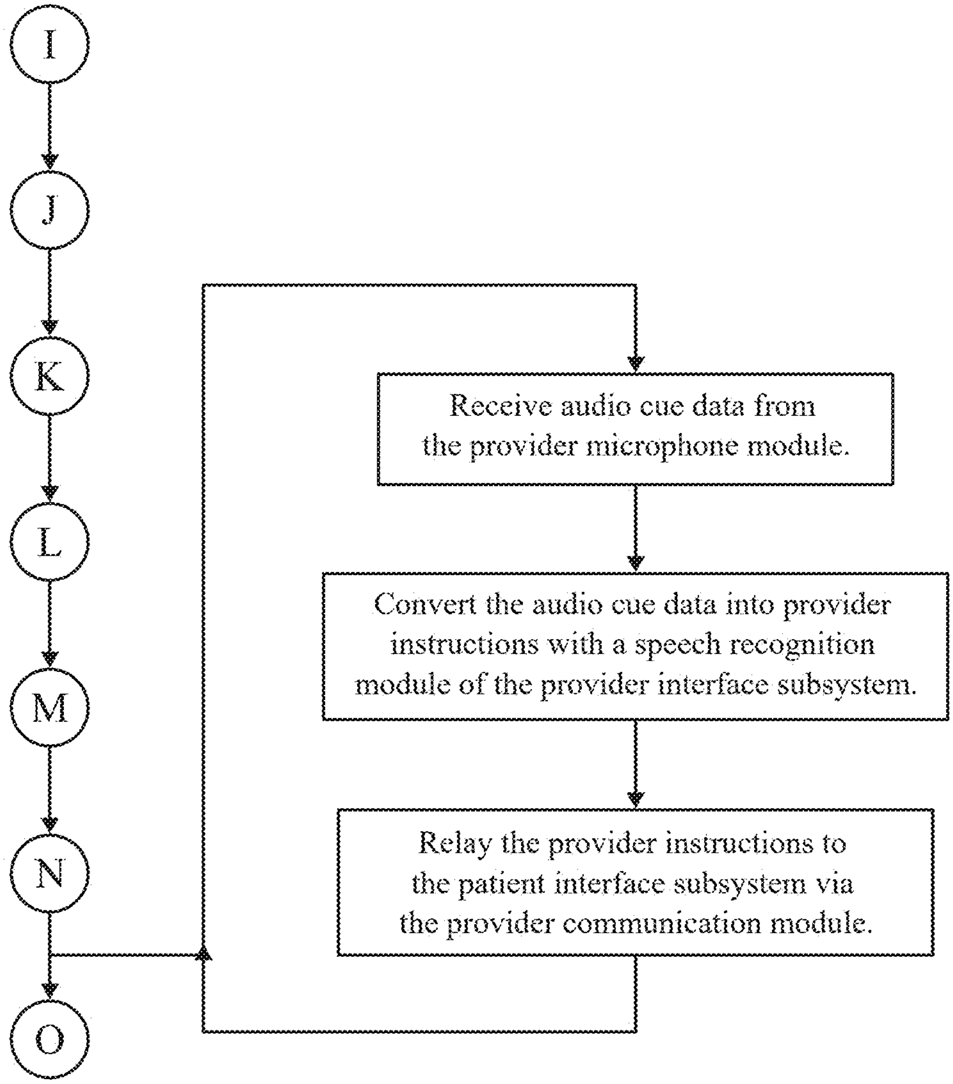
FIG. 26 is a flowchart showing the subprocess of converting audio cue data into provider instructions with a speech recognition module of the provider interface subsystem of the present invention.

In some embodiments, the audio cue data can be converted to a different format that can be transmitted to the patient interface subsystem and output in a non-audible format. As can be seen in FIG. 26, the provider processor can be further configured to receive audio cue data from the provider microphone module and convert the audio cue data into provider instructions with a speech recognition module of the provider interface subsystem. Further, the provider instructions are relayed to the patient interface subsystem via the provider communication module.

Figure 27:
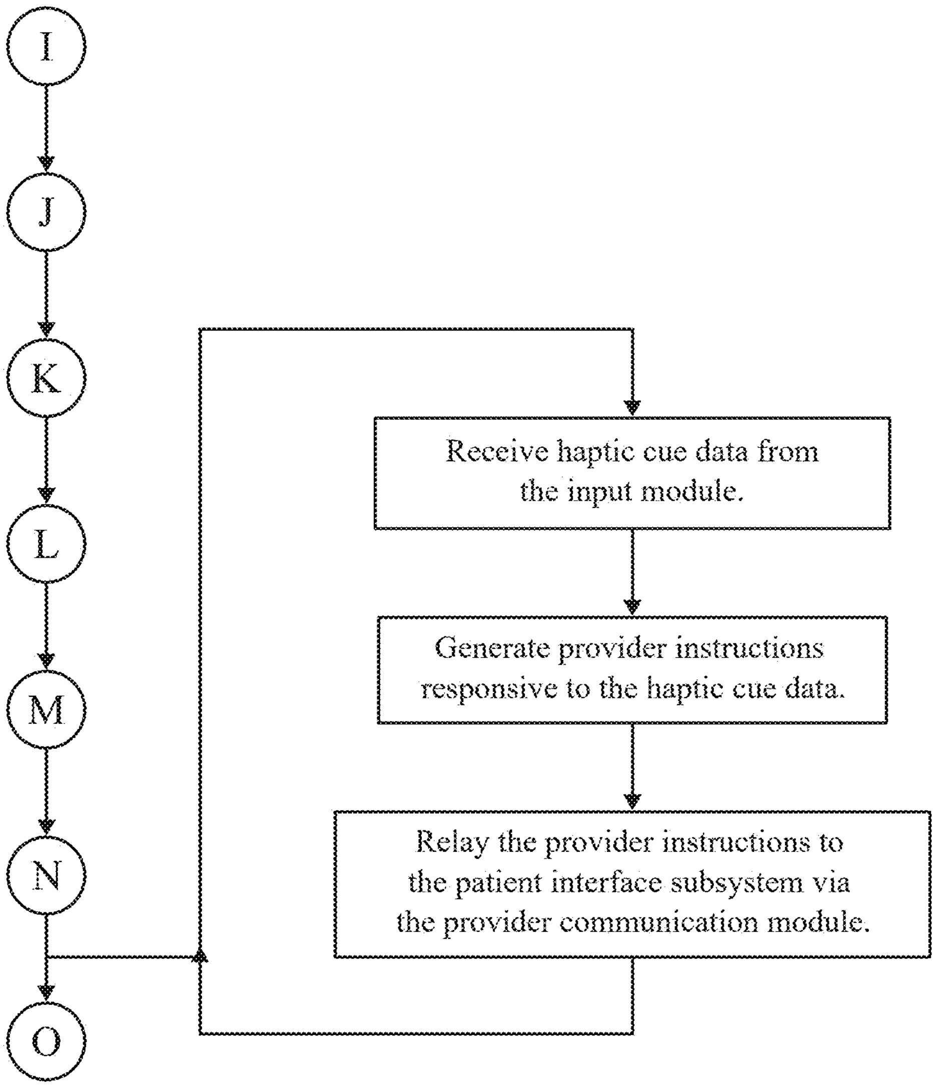
FIG. 27 is a flowchart showing the subprocess of capturing haptic cue data with the provider interface subsystem of the present invention.

In other embodiments, at least one provider processor may be further configured to receive haptic cue information from the input module, as can be seen in FIG. 27. The provider processor can be further configured to receive haptic cue data from the input module and generate provider instructions responsive to the haptic cue data. The provider instructions include data that can be used by the patient interface system. Further, the provider instructions are relayed to the patient interface subsystem via the provider communication module so that the corresponding haptic cues can be output to the patient. In other embodiments, the input module can be modified to receive different cue information.

Exemplary Embodiment of the Present Invention

Figure 6:
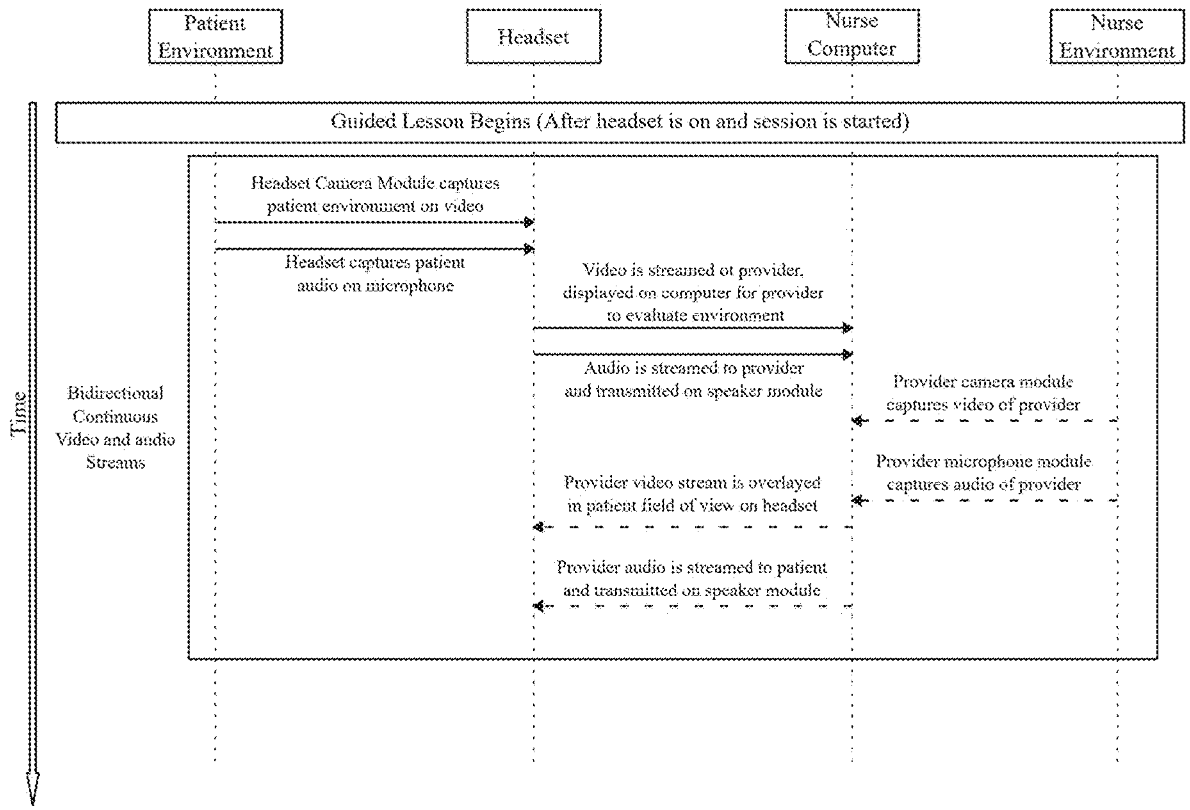
FIG. 6 is a diagram showing the overall process of the present invention.
Figure 7:
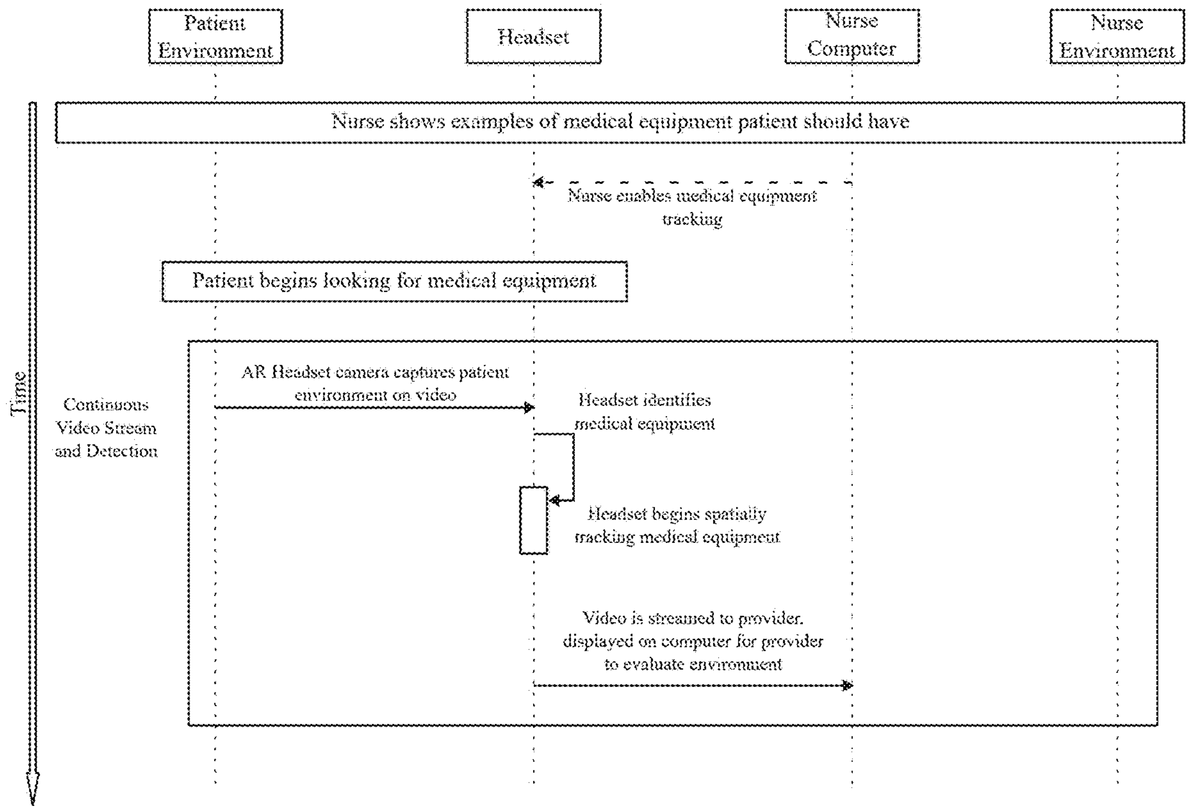
FIG. 7 is a continuation of the diagram shown in FIG. 6.
Figure 8:
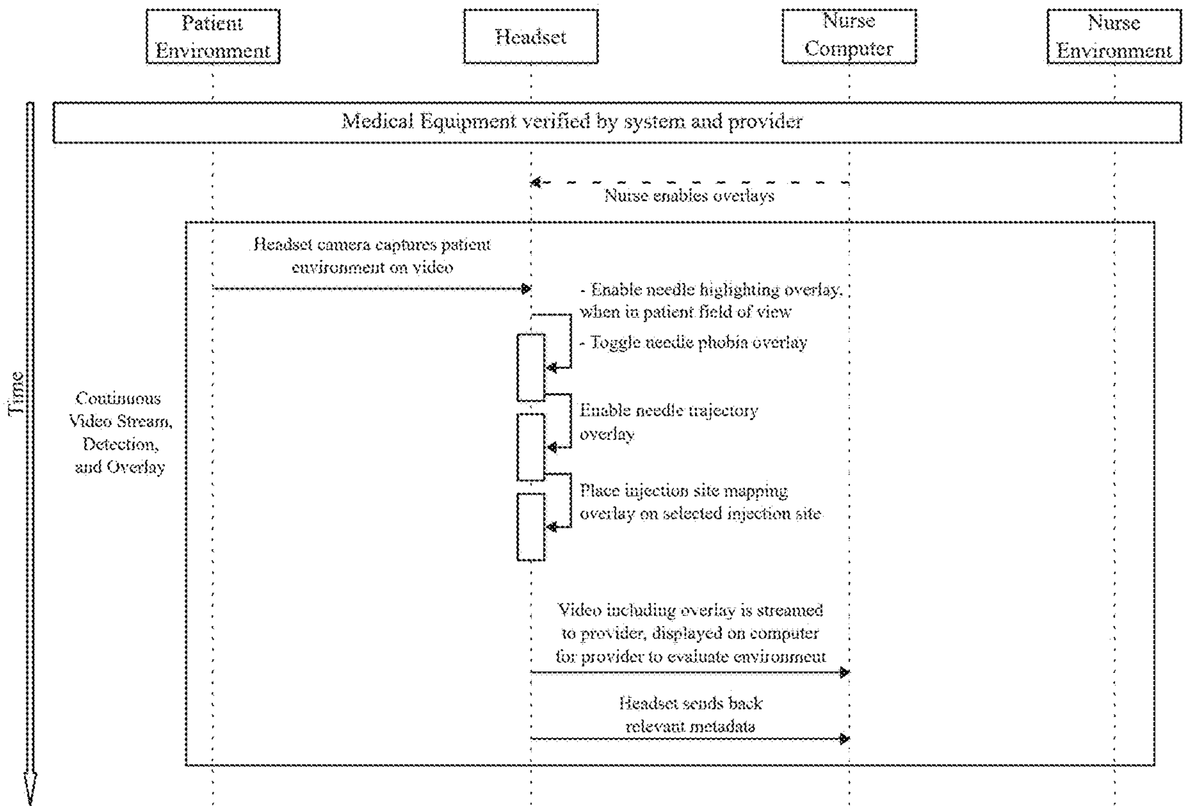
FIG. 8 is a continuation of the diagram shown in FIG. 7.
Figure 9:
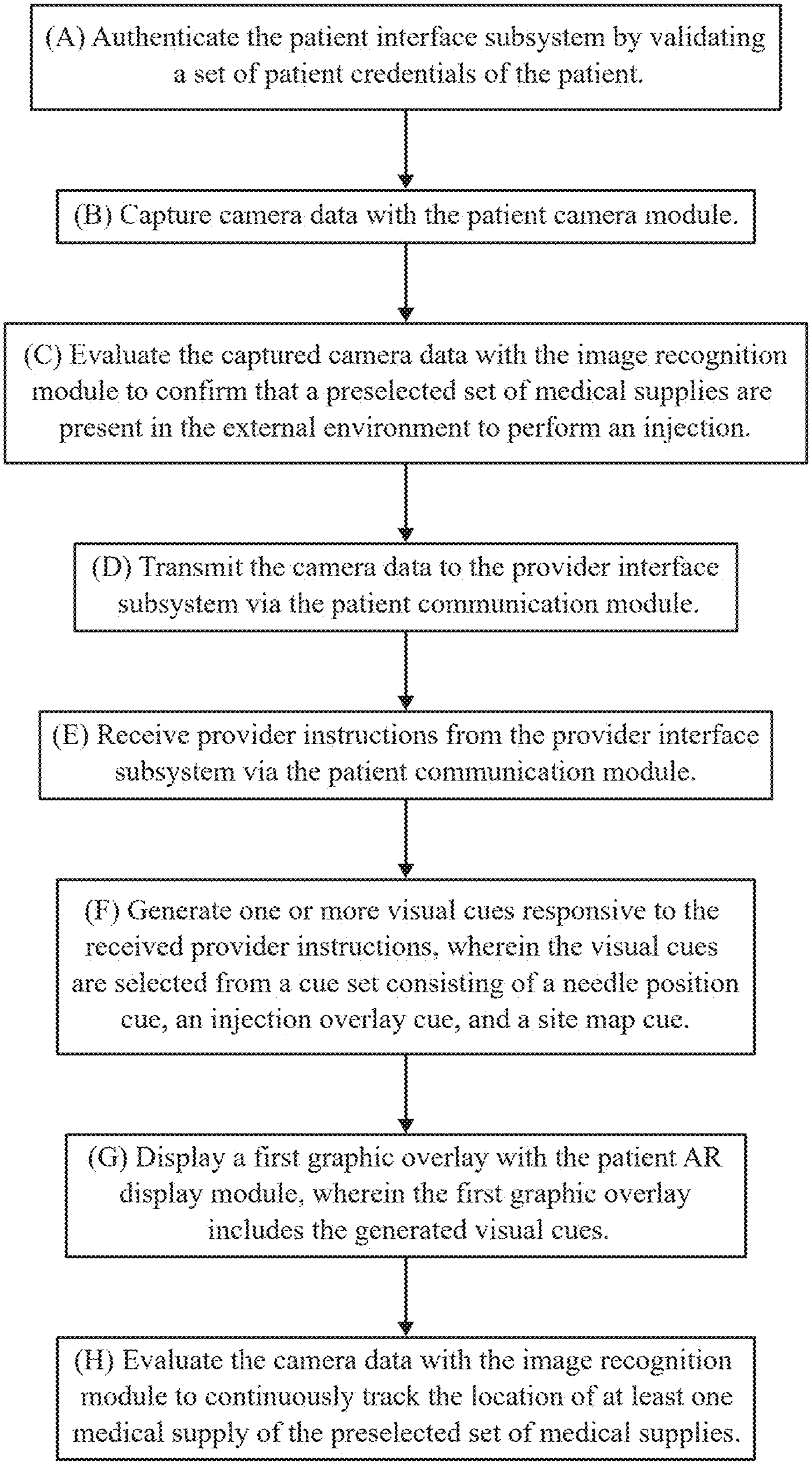
FIG. 9 is a flowchart showing the overall processes performed with the patient interface subsystem of the present invention.

In an exemplary embodiment, once a patient is leaving a doctor's office, the patient is provided with a software application that allows the patient to access the system of the present invention. As can be seen in FIGS. 6 through 8, the software application can be developed to operate in different operating systems on different computing devices. For example, the software application will be provided as a mobile application that can be installed on a smartphone. Further, the software application can include various administrative functions including, but not limited to, a scheduling feature that allows the scheduling of training sessions. For example, the patient can schedule an appointment with the pharmaceutical company to receive medical injection training at a desired date and time. Furthermore, the patient is provided with the patient interface subsystem, which is preferably an AR headset.

As can be seen in FIGS. 6 through 8, once the patient gets home, the patient can participate in a virtual training session with the AR headset to familiarize themselves with the AR capabilities of the headset. Once the training appointment has been set, the patient receives a notification reminder on the patient's smartphone that has the software application installed. To start the training session, the patient must provide the necessary patient credentials, such as a patient Identification (ID) number to maintain privacy laws (e.g., Health Insurance Portability and Accountability Act laws). After the patient credentials have been entered and validated, the healthcare provider receives a notification that the patient has entered the system and is waiting to link to the provider interface subsystem, which is preferably a computer workstation from where the healthcare provider can monitor the training session. Based on the patient credentials, the present invention can provide the healthcare provider with the necessary patient information for the training session via the provider's workstation, such as the patient's health records and the administration type for the patient. Furthermore, the system of the present invention can include preset packages that include various training tools for different medical procedures that can be relayed to the patient's AR headset during the training procedure.

As can be seen in FIGS. 6 through 8, the healthcare provider is prompted to launch the corresponding training package back to the patient headset via the provider's workstation. The healthcare provider then initializes connection to the patient's AR headset. The patient is prompted to put on the patient's AR headset to communicate with the healthcare provider. From here, the healthcare provider live streams directly from the provider's workstation. The live stream is visually displayed on the patient's AR headset. For example, if the patient is looking at a living room, the healthcare provider can be projected in the top right corner on the patient's AR headset overlay as if the healthcare provider is in the living room. While the patient is viewing the healthcare provider on the patient headset, the healthcare provider is preferably watching a live feed from the patient's line of vision on the provider's workstation. This way, the healthcare provider can monitor a patient's body and surroundings to guide the patient through the training. The patient's AR headset has a library of AR visuals that help guide the patient through any injection-based training. In addition, a series of live steps are available along the training session that allows the healthcare provider to walk the patient through keeping proper hygiene, assessing that the medical supplies are correct, drawing up medication into a syringe, and finally delivering the injection. The AR visuals ensure that the patient is receiving clear instructions.

Further, the healthcare provider is also able to send vibratory, auditory, and/or visual cues to the patient's AR headset to direct the patient on where to look and what to do while the patient's AR headset is also employing image recognition to automatically track medical supplies in the surroundings. These cues can be set manually or invoked via speech recognition which are then converted to cues. For example, the healthcare provider can say "please find the needle," and the patient's AR headset overlays an arrow pointing in the direction of the needle to advise the patient on the location. This helps the healthcare provider when communicating what medical device, medication, or injection site to look at.

Further, the patient's AR headset can recognize and help the patient identify different types of medical equipment by highlighting each device with a different color. For example, the medication may be highlighted green, but the needle or syringe can be highlighted yellow to show a patient very clearly what equipment should be picked up at each step. Once the patient is advised to draw up medication, the patient's AR headset tracks the fluid levels that are being drawn into the needle and highlights when a patient has drawn up the correct amount. AR visuals can also be deployed to show a patient proper needle techniques such as flicking the top of the needle to remove any air bubbles or using geometric figures to explain necessary angles for needle injection trajectory. Once the patient is ready to perform the injection, the healthcare provider can use other features of the patient's AR headset to monitor the patient's health vitals such as the patient's heart rate. This allows the healthcare provider to assess any potential allergic reactions that could occur during or post-injection.

In addition, the patient can have an epinephrine clasp which can also be linked to the patient headset. This allows the healthcare provider to remotely deliver a dosage of epinephrine if the patient's vitals begin indicating an allergic reaction. Other smart medical devices can also be connected to the system of the present invention. From here, the healthcare provider can approve the patient to begin the injection. The healthcare provider prompts the patient to look at the injection site which the patient can see on a grid mapped out over the injection site via the patient's AR headset. This is to show the overall injection site (all the injection sites for the patient's disease can be mapped out during the training session and stored in the patient's application for later usage to understand where the injection sites are, and how frequently the sites should be rotated). Now the patient is prompted by the healthcare provider to look for a red "X" on the injection site displayed by the patient's AR headset which corresponds to the true place of injection.

Further, the healthcare provider can explain to the patient that once the needle is over the "X" in the right spot, and at the right orientation, the "X" turns green on the patient's AR headset indicating that the patient can proceed to inject the medication. Another example of smart needle implementation with the patient's AR headset is to enable the needle's drug delivery system to prevent the injection administration until the red "X" has turned green. After the injection has been administered, the patient is advised to continue looking at the injection site for a length of time so that the patient's AR headset can analyze the hue of the skin to ensure there is no reaction to the injection. Finally, the healthcare provider can provide a set of visuals to walk the patient through disposing of any medical equipment no longer necessary.

Supplemental Method of the Present Invention

An overall process of a method of the present invention begins by providing at least one patient account managed by at least one remote server (Step A), wherein the patient account is associated with a corresponding patient AR system (patient interface subsystem). A plurality of healthcare provider accounts managed by the remote server are provided (Step B), wherein each healthcare provider account is associated with a corresponding provider PC device. Next, a video live feed with the corresponding patient AR system of the patient account (Step C), if a virtual procedure session is initiated between the corresponding patient AR system of the patient account and the corresponding provider PC device of at least one specific provider account. The specific provider account is from the plurality of healthcare provider accounts. Next, the video live feed is relayed from the corresponding patient AR system of the patient account to the corresponding provider PC device of the specific provider account (Step D). The video live feed is then output with the corresponding provider PC device of the specific provider account (Step E). Next, the specific provider account is prompted to enter at least one feed annotation for the video live feed with the corresponding provider PC device (Step F). The feed annotation is then relayed from the corresponding provider PC device of the specific provider account, and to the corresponding patient AR system of the patient account (Step G), if the graphical annotation is entered by the specific provider account. Further, the video live feed and the feed annotation is output with the corresponding patient AR system of the patient account (Step H). Finally, two-way audio communication is managed between the corresponding patient AR system of the patient account and the corresponding provider PC device of the specific provider account during Steps C through H (Step I). Further, the corresponding patient AR system preferably includes a patient AR headset and a patient mobile device.

A subprocess for establishing connection between the healthcare provider and the patient includes the steps of prompting the patient account to initiate the virtual procedure session with the corresponding patient AR system and mobile device. Next, the specific provider account is prompted to join the virtual procedure session with the corresponding provider PC device, if the virtual procedure session is initiated by the patient account. Then, Step C is executed, if the virtual procedure session is initiated by the patient account, and if the virtual procedure session is selected to be joined by the specific provider account.

Different types of annotations can be implemented. A subprocess for providing illustrative annotations includes the steps of prompting the specific provider account to draw at least one illustrative annotation with the corresponding provider PC device input module during Step F. Then, the illustrative annotation is designated as the feed annotation with the corresponding provider PC device of the specific provider account. Further, a subprocess for providing graphical annotations includes the steps of prompting the specific provider account to insert at least one graphical annotation with the corresponding provider PC device during Step F. Then, the graphical annotation is designated as the feed annotation with the corresponding provider PC device of the specific provider account. Further, a subprocess for providing textual annotations includes the steps of prompting the specific provider account to insert at least one textual annotation with the corresponding provider PC device during Step F. Then, the textual annotation is designated as the feed annotation with the corresponding provider PC device of the specific provider account. Furthermore, the subprocess of overlaying the different annotations includes the step of augmentedly overlaying the feed annotation onto the video live feed with the corresponding patient AR system of the patient account before Step H.

A subprocess of transmitting patient audio includes the steps of receiving at least one piece of patient audio with the corresponding patient AR system of the patient account during Step I. Next, the piece of patient audio is relayed from the corresponding patient AR system of the patient account and to the corresponding provider PC device of the specific provider account. Then, the piece of patient audio is output with the corresponding provider PC device of the specific provider account.

A subprocess of transmitting provider audio includes the steps of receiving at least one piece of provider audio with the corresponding provider PC device microphone module of the specific provider account during Step I. Next, the piece of provider audio is relayed from the corresponding provider PC device of the specific provider account and to the corresponding patient AR system of the patient account. Then, the piece of provider audio is output with the speaker module of the corresponding patient AR system of the patient account.

A subprocess of providing haptic cues includes the steps of providing the corresponding patient AR system with a haptics module. Next, the provider account is prompted to enter at least one haptic cue with the corresponding provider PC device during Step F. The haptic cue is then relayed from the corresponding provider PC device of the specific provider account and to the corresponding patient AR system of the patient account, if the haptic cue is entered by the specific provider account. Then, the haptic cue is output with the haptics module for the corresponding patient AR system of the patient account during Step H.

A subprocess of providing medical-supply visual references includes the steps of providing a plurality of medical-supply visual references stored on the corresponding patient AR system of the patient account. Next, the video live feed is compared to each medical-supply visual reference with the corresponding patient AR system of the patient account during Step D in order to identify at least one matching medical supply shown in the video live feed. Then, the matching medical supply shown in the video live feed is graphically highlighted with the corresponding patient AR system of the patient account before Step E, if the matching medical supply shown in the video live feed is identified by the corresponding patient AR system of the patient account.

A subprocess of providing anatomical visual references includes the steps of providing a plurality of anatomical visual references stored on the corresponding patient AR system of the patient account. Next, the video live feed is compared to each anatomical visual reference with the corresponding patient AR system of the patient account during Step D in order to identify at least one matching anatomical marker shown in the video live feed. Then, the matching anatomical marker shown in the video live feed is graphically highlighted with the corresponding patient AR system of the patient account before Step E, if the matching anatomical marker shown in the video live feed is identified by the corresponding patient AR system of the patient account.

A subprocess of implementing health-monitoring devices includes the steps of providing the corresponding patient AR system with at least one health-monitoring sensor. Next, at least one piece of health data for the patient account is captured with the health-monitoring sensor for the corresponding patient AR system. Further, the piece of health data is relayed from the corresponding patient AR system of the patient account to the corresponding provider PC device of the specific provider account. Then, the piece of health data is output with the corresponding provider PC device of the specific provider account during Step E.

A subprocess of implementing patient records includes the steps of providing the patient account with a plurality of patient records managed by the remote server. Next, the specific provider account is prompted to view at least one specific record from the plurality of patient records with the corresponding provider PC device. Then, the specific record is output with the corresponding provider PC device of the specific provider account during Step E, if the specific record is selected to be viewed by the specific provider account.

Although the invention has been explained in relation to its preferred embodiment, it is to be understood that many other possible modifications and variations can be made without departing from the spirit and scope of the invention.

What is claimed is:

1. A system comprising:

a patient interface subsystem associated with a patient;

a patient communication module configured to enable the communication between the patient interface subsystem and a provider interface subsystem;

a patient processor operatively coupled to the patient interface subsystem and the patient communication module, and wherein the patient processor is configured to:

evaluate camera data that includes scene information of an external environment of the patient to confirm that a set of medical supplies are present in the external environment;

receive provider instructions of a remote healthcare provider from the provider interface subsystem via the patient communication module;

generate, in real time, one or more dynamic visual cues responsive to the received provider instructions;

cause display of a first graphic overlay with a patient augmented reality display module, wherein the first graphic overlay includes the generated one or more dynamic visual cues to be superimposed on a field of vision of the patient in real time; and evaluate additional camera data of either a given medical supply of the set of medical supplies or information regarding the patient.

2. The system of claim 1, wherein the provider instructions correspond to a virtual training session for the patient.

3. The system of claim 1, wherein the provider instructions are configured to guide the patient to find a particular one of the set of medical supplies.

4. The system of claim 1, wherein the provider instructions are configured to virtually train the patient to perform a medical procedure.

5. The system of claim 4, wherein the medical procedure includes an injection operation.

6. The system of claim 1, wherein the one or more visual cues are selected from a cue set.

7. The system of claim 6, wherein the cue set further includes at least one audible cue.

8. The system of claim 6, wherein the cue set further includes at least one haptic cue.

9. The system of claim 1, wherein the generated one or more dynamic visual cues to be superimposed on a field of vision of the patient are configured to guide a user to perform an injection.

10. The system of claim 1, wherein the evaluation of the additional camera data determines one or more variables to be monitored during a training session.

11. The system of claim 1, wherein the set of medical supplies includes medical equipment.

12. The system of claim 1, wherein the evaluation of the additional camera data is used to track the given medical supply.

13. The system of claim 1, wherein the evaluation of the additional camera data is used to track the information regarding the patient.

14. A method comprising:

evaluating, by a patient processor, camera data that includes scene information of an external environment of a patient to confirm that a set of medical supplies are present in the external environment;

receiving, by the patient processor, provider instructions of a remote healthcare provider from a provider interface subsystem via a patient communication module;

generating, by the patient processor in real time, one or more dynamic visual cues responsive to the received provider instructions; and causing, by the patient processor, display of a first graphic overlay with a patient augmented reality display module, the first graphic overlay including the generated one or more visual cues to be superimposed on a field of vision of the patient in real time.

15. The method of claim 14, further comprising evaluating, by the patient processor, additional camera data of either a given medical supply of the set of medical supplies or information regarding the patient.

16. The method of claim 15, wherein evaluating the additional camera data includes determining one or more variables to be monitored during a patient training session.

17. The method of claim 15, wherein evaluating the additional camera data is used to either track the given medical supply or track the information regarding the patient.

18. The method of claim 15, wherein the generated one or more dynamic visual cues to be superimposed on a field of vision of the patient are configured to guide a user to perform an injection.

19. The method of claim 18, wherein the user is the patient.

20. The method of claim 14, wherein the provider instructions are configured to either guide the patient to find a particular one of the set of medical supplies, or to virtually train the patient to perform a medical procedure.

* * * * *